US010039491B2

(12) United States Patent
Thompson et al.

(10) Patent No.: US 10,039,491 B2
(45) Date of Patent: Aug. 7, 2018

(54) METHODS FOR REDUCING NOISE IN OPTICAL BIOLOGICAL SENSORS

(71) Applicant: Verily Life Sciences LLC, Mountain View, CA (US)

(72) Inventors: Jason Donald Thompson, Palo Alto, CA (US); Vikram Singh Bajaj, Mountain View, CA (US); Victor Marcel Acosta, San Francisco, CA (US); Tamara Lynn Troy, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 467 days.

(21) Appl. No.: 14/319,182

(22) Filed: Jun. 30, 2014

(65) Prior Publication Data

US 2015/0382105 A1  Dec. 31, 2015

(51) Int. Cl.
*A61B 5/1455* (2006.01)
*A61B 5/00* (2006.01)

(52) U.S. Cl.
CPC .......... *A61B 5/6801* (2013.01); *A61B 5/1455* (2013.01); *A61B 5/681* (2013.01); *A61B 5/7203* (2013.01); *A61B 5/7475* (2013.01)

(58) Field of Classification Search
CPC .............. A61B 5/1455; A61B 5/14551; A61B 5/14556; A61B 5/68; A61B 5/6801; A61B 5/681; A61B 5/72; A61B 5/7203
See application file for complete search history.

(56) References Cited

U.S. PATENT DOCUMENTS 4,178,917 A * 12/1979 Shapiro .............. A61B 5/14556
600/322
5,325,865 A  7/1994 Beckman et al.
(Continued)

FOREIGN PATENT DOCUMENTS

WO  2008140624 A2  11/2008
WO  2013028784 A1  2/2013
WO  2013165888 A2  11/2013

OTHER PUBLICATIONS

International Search Report and Written Opinion of International Application No. PCT/US2015/034243 dated Sep. 3, 2015 (dated Sep. 3, 2015).

(Continued)

*Primary Examiner* — Eric Winakur
(74) *Attorney, Agent, or Firm* — McDonnell Boehnen Hulbert & Berghoff LLP

(57) ABSTRACT

Optical measurement of physiological parameters with wearable devices often includes measuring signals in the presence of significant noise sources. These noise sources include, but are not limited to, noise associated with: variable optical coupling to skin or tissue, variations in tissue optical properties with time due to changes in humidity, temperature, hydration, variations in tissue optical properties between individuals, variable coupling of ambient light sources into detectors, and instrument and detector noise, including electrical noise, radio frequency or magnetic interference, or noise caused by mechanical movement of the detector or its components. The present disclosure includes devices and methods configured to produce representations of the raw data in which noise, broadly defined, is separated from the data of interest. The disclosed devices and methods (Continued)

may include subtracting or calibrating out these noise sources and other spurious fluctuations in wearable devices with optical sensors.

14 Claims, 16 Drawing Sheets

(56) References Cited

U.S. PATENT DOCUMENTS

| | | | |
|---|---|---|---|
| 6,615,063 | B1 | 9/2003 | Ntziachristos et al. |
| 8,449,471 | B2 | 5/2013 | Tran |
| 8,738,107 | B2 * | 5/2014 | Markle .............. A61B 5/14532 |
| | | | 600/316 |
| 2006/0165805 | A1 | 7/2006 | Steinhoff et al. |
| 2010/0231909 | A1 | 9/2010 | Trainer |
| 2012/0179011 | A1 | 7/2012 | Moon et al. |
| 2013/0286379 | A1 | 10/2013 | Li et al. |

OTHER PUBLICATIONS

M.E. Dickinson et al., "Multi-Spectral Imaging and Linear Unmixing Add a Whole New Dimension to Laser Scanning Fluorescence Microscopy", BioTechniques, vol. 31, No. 6, pp. 1272-1278 (2001).

\* cited by examiner

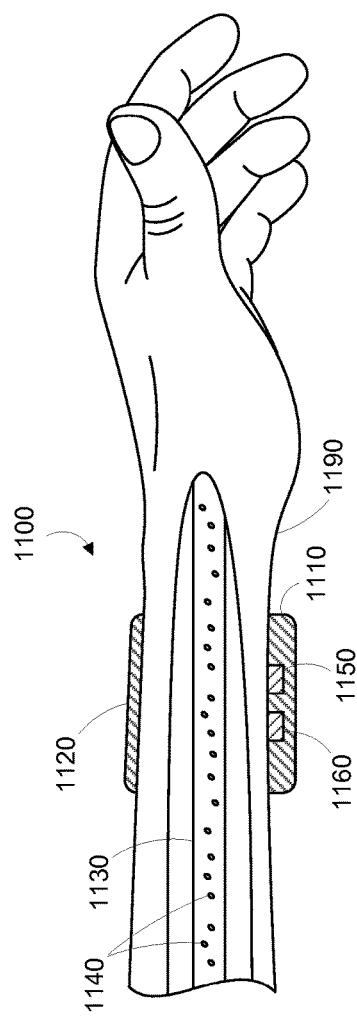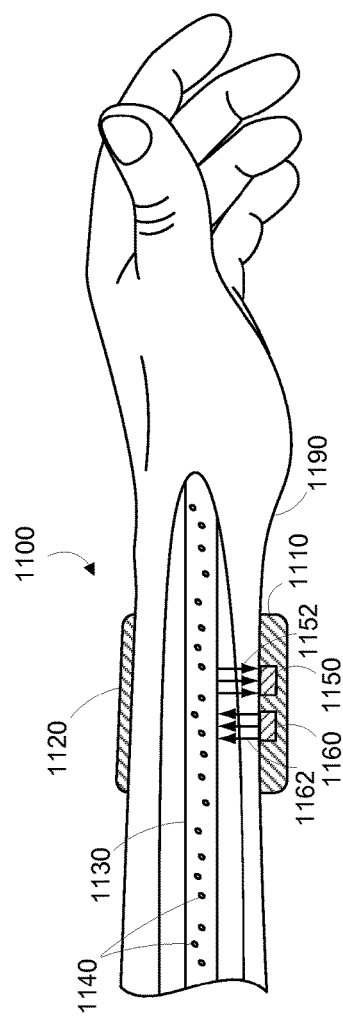
FIGURE 11A
FIGURE 11B

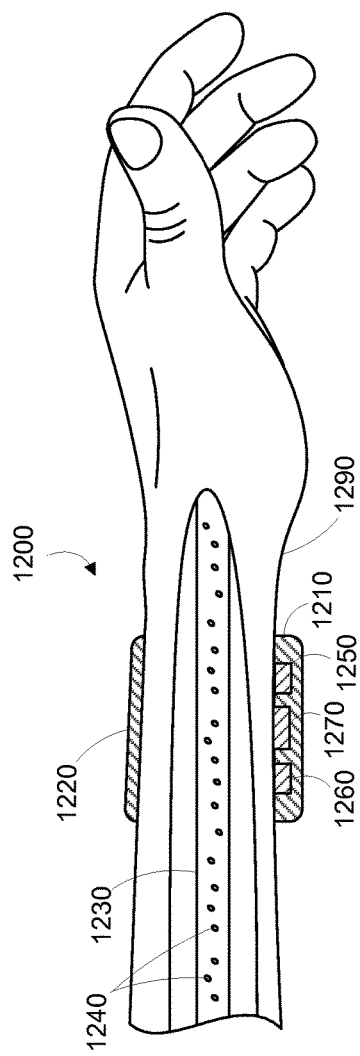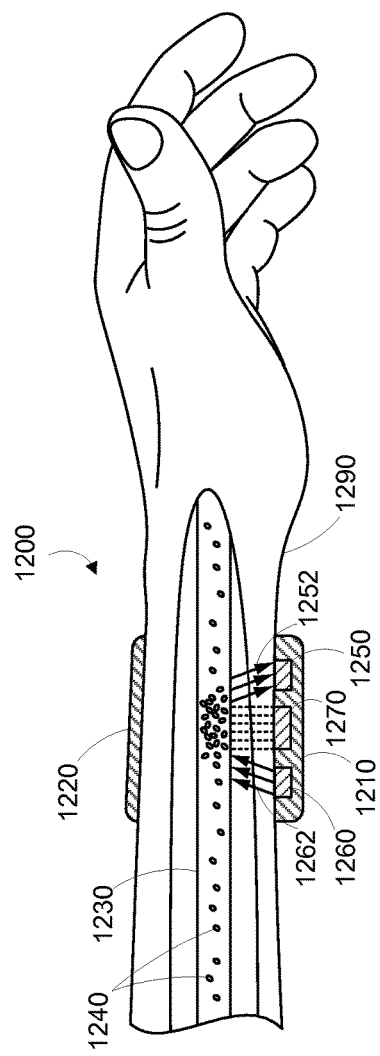

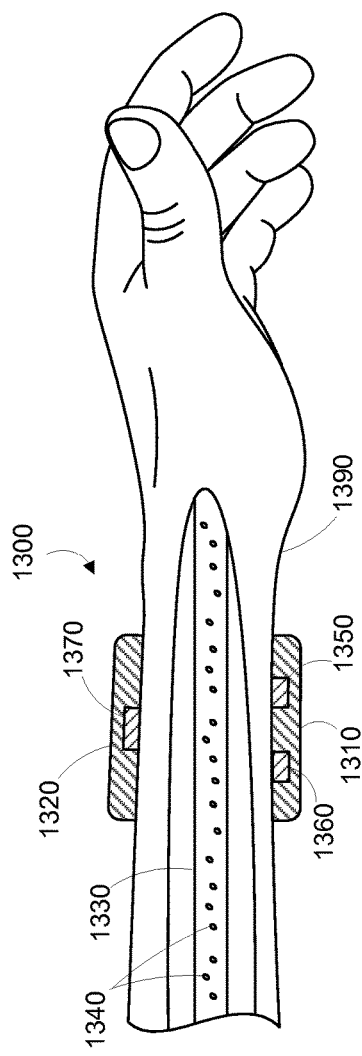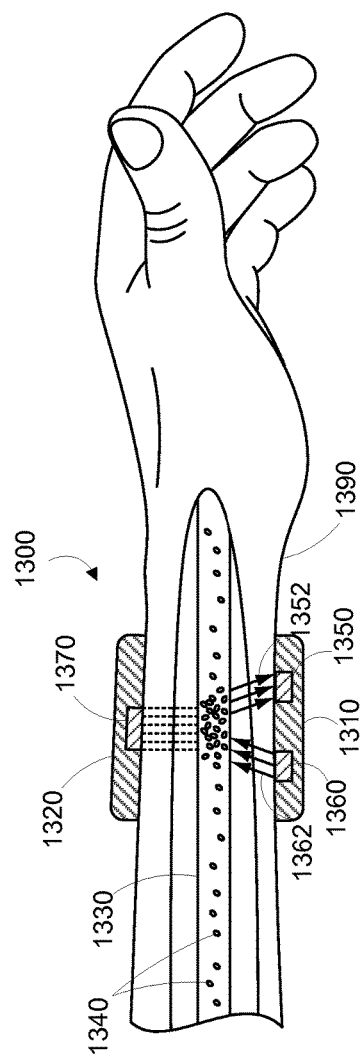

METHODS FOR REDUCING NOISE IN OPTICAL BIOLOGICAL SENSORS

BACKGROUND

Unless otherwise indicated herein, the materials described in this section are not prior art to the claims in this application and are not admitted to be prior art by inclusion in this section.

A number of scientific methods have been developed in the medical field to evaluate physiological conditions of a person by detecting and/or measuring one or more analytes in a person's blood or other bodily fluids or tissues. The one or more analytes could be any analytes that, when present in or absent from the blood, or present at a particular concentration or range of concentrations, may be indicative of a medical condition or health state of the person. The one or more analytes could include enzymes, reagents, hormones, proteins, cells or other molecules, such as carbohydrates, e.g., glucose.

In a typical scenario, a person's blood is drawn and either sent to a lab or input into a handheld testing device, such as a glucose meter, where one or more tests are performed to measure various analyte levels and parameters in the blood. For most people, the blood tests are infrequent, and an abnormal analyte level indicative of a medical condition may not be identified until the next blood test is performed. Even in the case of relatively frequent blood testing, such as may be found with those with diabetes, who regularly draw blood to test for blood glucose concentration, those blood tests are typically performed when the user is awake, although the blood glucose levels (and potential variations in such levels) occurring during the night could provide important information to assist a physician in assessing that person's medical condition. Further, most known methods of analyte detection and analysis require the collection of blood or other bodily fluid samples, which may be inconvenient, invasive and require significant patient compliance.

Moreover, some blood analytes are particularly difficult to identify and quantify with conventional sensing techniques. For small or rarified analytes, such as circulating tumor cells, for example, only 1 such cell may be present in 10 mL of blood. Impractically large quantities of blood would have to be drawn or otherwise sampled and analyzed in order to catch such cells with statistical significance.

Methods for analyte detection and characterization often suffer from a low signal-to-noise ratio (SNR), since the signal obtained from the analyte (in general, a small object) is typically weak in comparison to the background. This can make discerning between target analytes present in the blood, versus other analytes, particles, and tissues, etc. present in the blood and elsewhere in the body can be very difficult, especially where the measurements are taken non-invasively from outside the body. This is particularly true with some methods of analyte characterization, such as optical methods, or where the target analytes are rare in the blood or are of a relatively small size. Accordingly, such measurements can be much more time consuming (if a large volume of blood must be analyzed), less sensitive, less specific and generally less informative on the whole. For example, with fluorescence detection techniques, it is often difficult to obtain highly sensitive measurements of a target analyte because other tissues, cells, and molecules in the body may have some inherent fluorescent properties, creating a high level of background noise.

SUMMARY

In a first aspect, a method is provided. The method includes providing, in a wearable medical diagnostic device, a first and a second optical signal transmitted from within a lumen of subsurface vasculature. The first optical signal includes an unfiltered target signal and a first noise signal. The second optical signal includes a second noise signal. The first and second noise signals are correlated and a quotient of the unfiltered target signal and the first noise signal includes an unfiltered signal to noise ratio. The method further includes determining a filtered signal, based at least on the unfiltered target signal, the first noise signal, and the second noise signal. The filtered signal includes a filtered target signal and a filtered noise signal. A quotient of the filtered target signal and the filtered noise signal includes a filtered signal to noise ratio in which the filtered signal to noise ratio is higher than the unfiltered signal to noise ratio.

In a second aspect, a wearable medical diagnostic device is provided. The wearable medical diagnostic device includes at least one detector and a computing device. The at least one detector is configured to provide an unfiltered target signal, a first noise signal, and a second noise signal. The unfiltered target signal is transmitted substantially from within a lumen of subsurface vasculature. The first and second noise signals are correlated and a quotient of the unfiltered target signal and the first noise signal includes an unfiltered signal to noise ratio. The computing device is configured to determine a filtered signal, based at least on the unfiltered target signal, the first noise signal, and the second noise signal. The filtered signal includes a filtered target signal and a filtered noise signal. A quotient of the filtered target signal and the filtered noise signal includes a filtered to noise ratio in which the filtered signal to noise ratio is higher than the unfiltered signal to noise ratio.

In a third aspect, a non-transitory computer readable medium is provided. The non-transitory computer readable medium includes instructions executable by a computing device to cause the computing device to perform functions, the functions including receiving, in a wearable medical diagnostic device, a first and a second optical signal transmitted from within a lumen of subsurface vasculature. The first optical signal includes an unfiltered target signal and a first noise signal. The second optical signal includes a second noise signal. The first and second noise signals are correlated. The quotient of the unfiltered target signal and the first noise signal includes an unfiltered signal to noise ratio. The functions further include determining a filtered signal, based at least on the unfiltered target signal, the first noise signal, and the second noise signal. The filtered signal includes a filtered target signal and a filtered noise signal. A quotient of the filtered target signal and the filtered noise signal includes a filtered signal to noise ratio in which the filtered signal to noise ratio is higher than the unfiltered signal to noise ratio.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 11A is a side partial cross-sectional view of a wrist-mounted device, while on a human wrist, according to an illustrative embodiment.

FIG. 11B is a side partial cross-sectional view of a wrist-mounted device, while on a human wrist, according to an illustrative embodiment.

FIG. 12A is a side partial cross-sectional view of a wrist-mounted device, while on a human wrist, according to an illustrative embodiment.

FIG. 12B is a side partial cross-sectional view of a wrist-mounted device, while on a human wrist, according to an illustrative embodiment.

FIG. 13A is a side partial cross-sectional view of a wrist-mounted device, while on a human wrist, according to an illustrative embodiment.

FIG. 13B is a side partial cross-sectional view of a wrist-mounted device, while on a human wrist, according to an illustrative embodiment.

DETAILED DESCRIPTION

Figure 1:
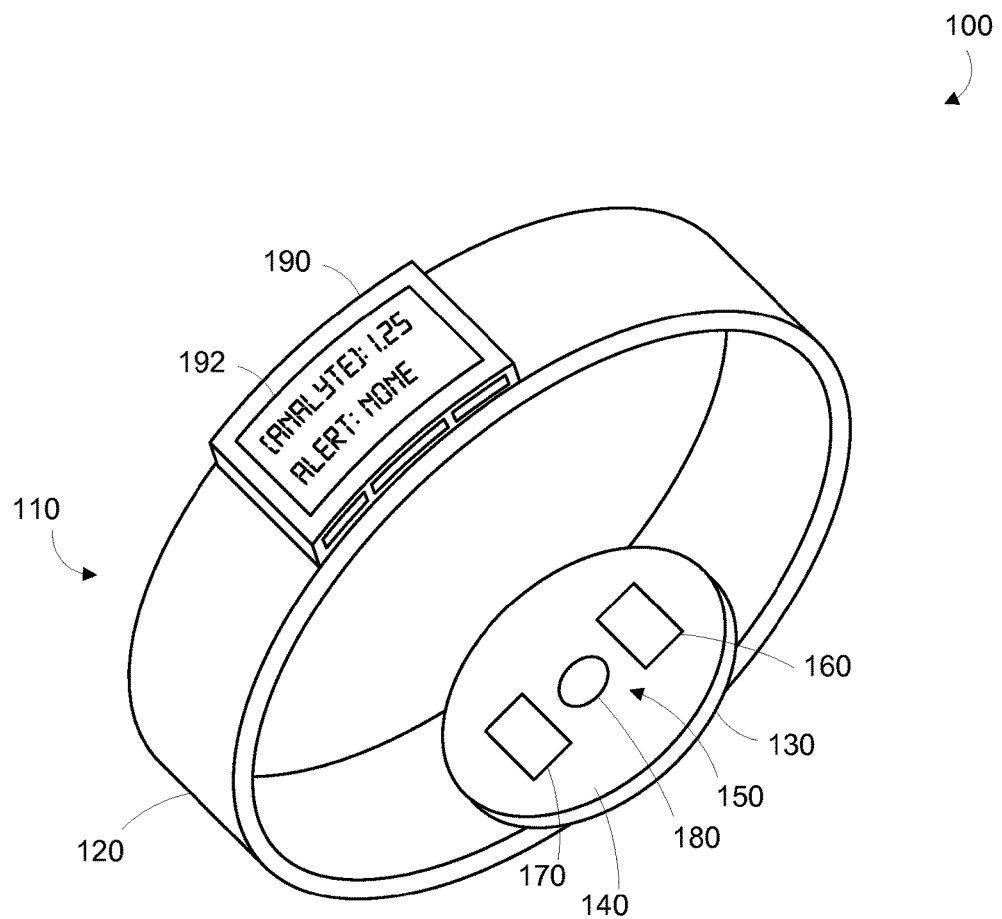
FIG. 1 is a perspective view of an example wearable device, according to an illustrative embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. OVERVIEW

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include enzymes, hormones, proteins, cells, or other molecules.

In an example embodiment, the system obtains at least some of the health-related information by detecting the binding or interaction of a clinically-relevant analyte to or with particles, for example, microparticles or nanoparticles, introduced into a lumen of the subsurface vasculature that have been functionalized with a receptor that has a specific affinity to bind to or interact with the specific analyte. The term "binding" is understood in its broadest sense to also include a detectable interaction between the clinically-relevant analyte and the functionalized particles. The functionalized particles can be introduced into the person's blood stream by injection, ingestion, inhalation, transdermally, or in some other manner.

The particles can be functionalized by covalently or otherwise attaching or associating a receptor that specifically binds or otherwise interacts with a particular clinically-relevant analyte. The functionalized receptor may be an antibody, peptide, nucleic acid, phage, bacteria, virus, aptamer or any other molecule with a defined affinity for a target analyte. Additionally or alternatively, the receptor may be inherent to the particle itself. For example, the particle itself may be a virus or a phage with an inherent affinity for certain analytes. Other compounds or molecules, such as fluorophores or autofluorescent or luminescent markers or non-optical contrast agents (e.g. acoustic impedance contrast, RF contrast and the like), which may assist in interrogating the particles in vivo, may also be attached to the particles.

The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, tryptophan, a virus, a phage, etc. Further, a particle may be of any shape, for example, spheres, rods, non-symmetrical shapes, etc.

In some examples, the particles may also be magnetic and can be formed from a paramagnetic, super-paramagnetic or ferromagnetic material or any other material that responds to a magnetic field. Alternatively, the particles may also be made of non-magnetic materials such as polystyrene. Where magnetic particles are used, the system may include a magnet that can direct into the portion of subsurface vasculature a magnetic field that is sufficient to manipulate functionalized magnetic particles in a lumen of that portion of subsurface vasculature, for example, to collect or slow down in a certain area. However, measurements may be taken without localized "collection" of the functionalized particles. The system may be configured to activate the magnetic field periodically, such as at certain times of the day (e.g., every hour).

The system may further include one or more data collection systems for interrogating, in a non-invasive manner, a target analyte present in a lumen of the subsurface vasculature in a particular local area. For example, the system may include a detector configured to detect a response signal transmitted from a portion of subsurface vasculature. The response signal may include both an analyte response signal and a background noise signal.

In an example embodiment, the analyte response signal could include light emitted from the target analyte. For example, the target analyte may include a chemiluminescent marker, such as a fluorophore, configured to produce a response signal in the form of light. The analyte response signal may include light emitted in response to a chemical reaction and/or biological interaction.

In some examples, the system may also include an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal may be any kind of signal that is benign to the patient, and may such as electromagnetic, magnetic, optic, acoustic, thermal, mechanical, or electric. An interaction, for example between the interrogating signal and the portion of subsurface vasculature, may result in a response signal that may be used to measure a physiological parameter or, more particularly, that may detect and/or measure the presence of the clinically-relevant analyte and/or the binding or interaction between the analyte and other chemical or biological elements.

In an illustrative embodiment, the analyte response may be related to an interaction between one or more target analytes and the interrogating signal source. For example, the interrogating signal source could include a light emitting diode or laser. The interrogating signal source may be configured to emit within narrow or wide bands throughout the electromagnetic spectrum. The target analyte may include a fluorophore. The fluorophore may be configured to emit light in response to excitation from the interrogating signal source. The light emitted from the fluorophore may represent the analyte response signal. The analyte response signal may occur anywhere in the electromagnetic spectrum.

For example, the interrogating signal may include a radio frequency (RF) signal and the response signal is a magnetic resonance signal, such as nuclear magnetic resonance (NMR). In another example, where the functionalized particles include a fluorophore, the interrogating signal may be an optical signal with a wavelength that can excite the fluorophore and penetrate the skin or other tissue and subsurface vasculature (e.g., a wavelength in the range of about 500 to about 1000 nanometers). The response signal may include fluorescence radiation from the fluorophore that can penetrate the subsurface vasculature and tissue to reach the detector. In another example, where the functionalized particles include an electrically conductive material or a magnetically lossy material, the interrogation signal may be a time-varying magnetic field or a radio frequency (RF) electromagnetic signal, with sufficient signal power to rapidly heat the particles. The response signal may be an acoustic emission from the particles, caused by rapid thermal expansion of the particles, or caused by cavitation of the liquid medium in contact with the particles.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to functionalized particles bound to or interacting with target analyte(s)—and an "unbound" particle signal—related to functionalized particles not bound to or interacting with target analyte(s). For example, in some measurement or characterization schemes, it may be useful or necessary to determine the percentage of functionalized particles introduced into the body that have bound to the target analyte. In such cases, the modulation source may be configured to modulate the analyte response signal differently than the unbound particle signal.

The elements of the system, namely the type of modulation, the type/shape/materials of particles, types of receptors and target analytes may all be interrelated. Ultimately, the type of particle and receptor used to detect a particular target analyte may be dictated, to some extent, by the characteristics of the target analyte (i.e., type, size, shape, affinities, etc.), the chosen type of modulation (i.e., spatial, spectral, thermal, magnetic, mechanical, chemical, etc.), and the mode of interrogation (optical, acoustic, magnetic, RF, etc.).

Data collected by the detector may be sent to a processor for analysis. The processor may be configured to non-invasively detect the one or more target analytes by differentiating the analyte response signal from the background noise signal based, at least in part, on the modulation. In some cases where the analyte includes a bound particle, the processor may further be configured to differentiate the analyte response signal from the unbound particle signal.

The processor may be configured to determine the concentration of a particular target analyte in the blood from, at least in part, the analyte response signal. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the nutritional analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has experienced certain adverse health conditions, such as a migraine or a heart attack, when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

In an illustrative embodiment, the processor and/or other elements of the system may be configured in an effort to optimize signal to noise ratio. For example, the system may be configured to compare two or more signal channels whose noise is correlated. One of the signal channels may substantially contain the signal of interest, while each of the signal channels may contain well-correlated noise signals. Through subtraction, division, and/or other signal processing algorithms, a signal of interest may be separated from the noise signals, which may result in a higher signal to noise ratio.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. ILLUSTRATIVE WEARABLE DEVICES

A wearable device 100 may automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. may be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which may include one or more parameters that may relate to the health of the person wearing the wearable device. For example, the detector 160 could be configured to measure blood pressure, pulse rate, respiration rate, skin temperature, etc. At least one of the detectors 160 may be configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal through the surface of the wearer's skin into the portion of subsurface vasculature, for example, into a lumen of the subsurface vasculature. The interrogating signal may be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector. Alternatively, the interrogating signal may include electromagnetic radiation with wavelengths outside the 400-1600 nm range.

In some cases, an interrogating signal is not necessary to measure one or more of the physiological parameters and, therefore, the wearable device 100 need not include a signal source 170. For example, the functionalized particles may include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemiluminescent marker configured to produce a response signal in the form of luminescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 may be configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
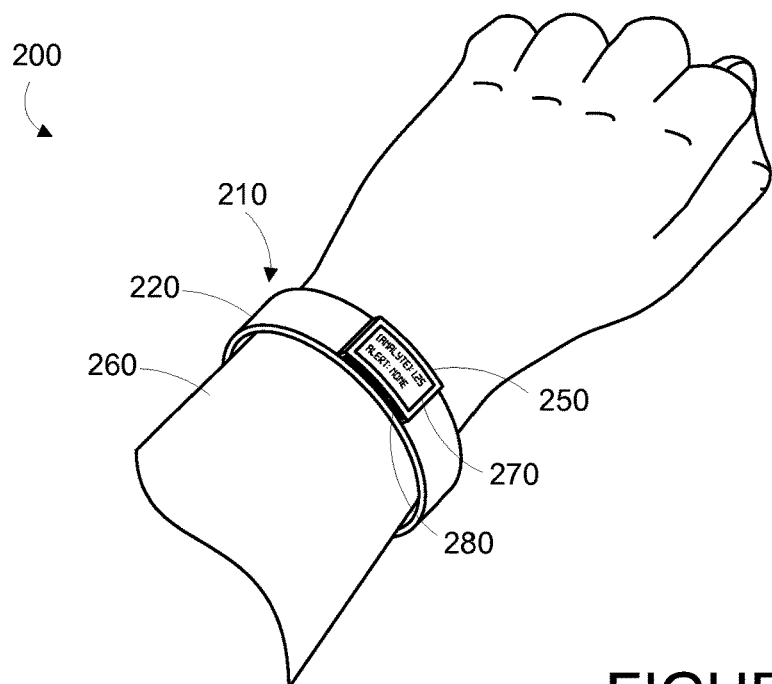
FIG. 2A is a perspective top view of an example wrist-mounted device, when mounted on a wearer's wrist, according to an illustrative embodiment.
Figure 2B:
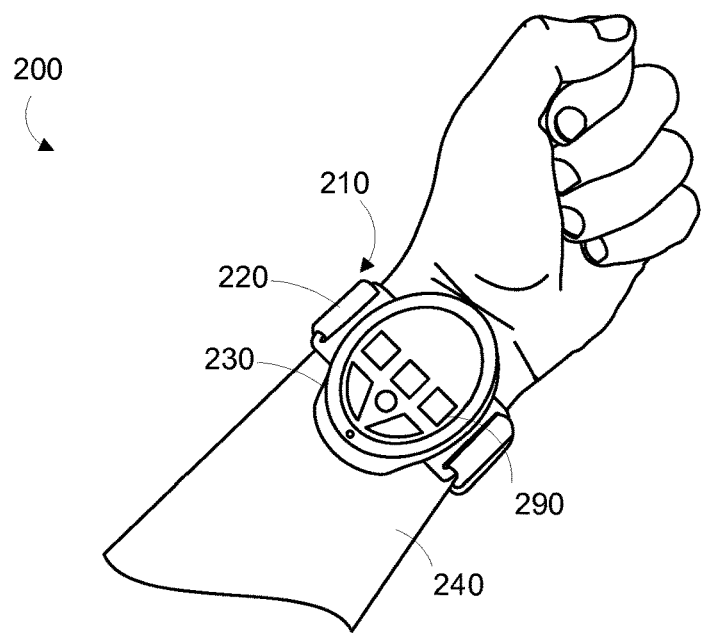
FIG. 2B is a perspective bottom view of an example wrist-mounted device shown in FIG. 2A, when mounted on a wearer's wrist, according to an illustrative embodiment.

In one example, the wearable device is provided as a wrist-mounted device, as shown in FIGS. 2A, 2B, 3A-3C, 4A, 5, and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
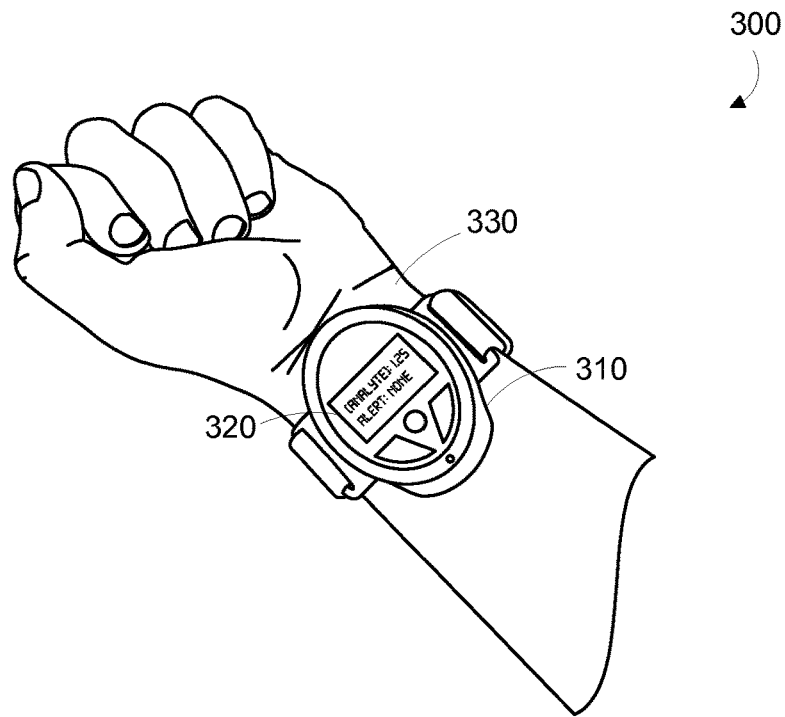
FIG. 3A is a perspective bottom view of an example wrist-mounted device, when mounted on a wearer's wrist, according to an illustrative embodiment.
Figure 3B:
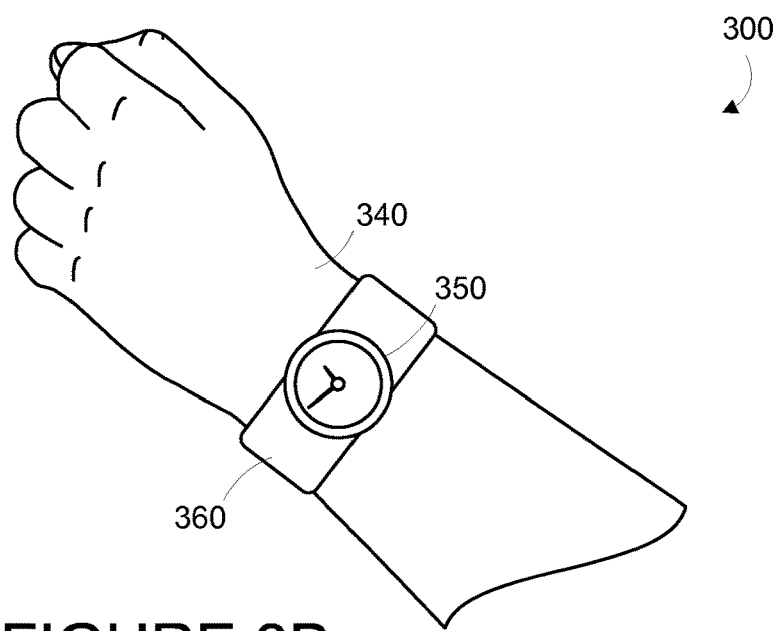
FIG. 3B is a perspective top view of an example wrist-mounted device shown in FIG. 3A, when mounted on a wearer's wrist, according to an illustrative embodiment.
Figure 3C:
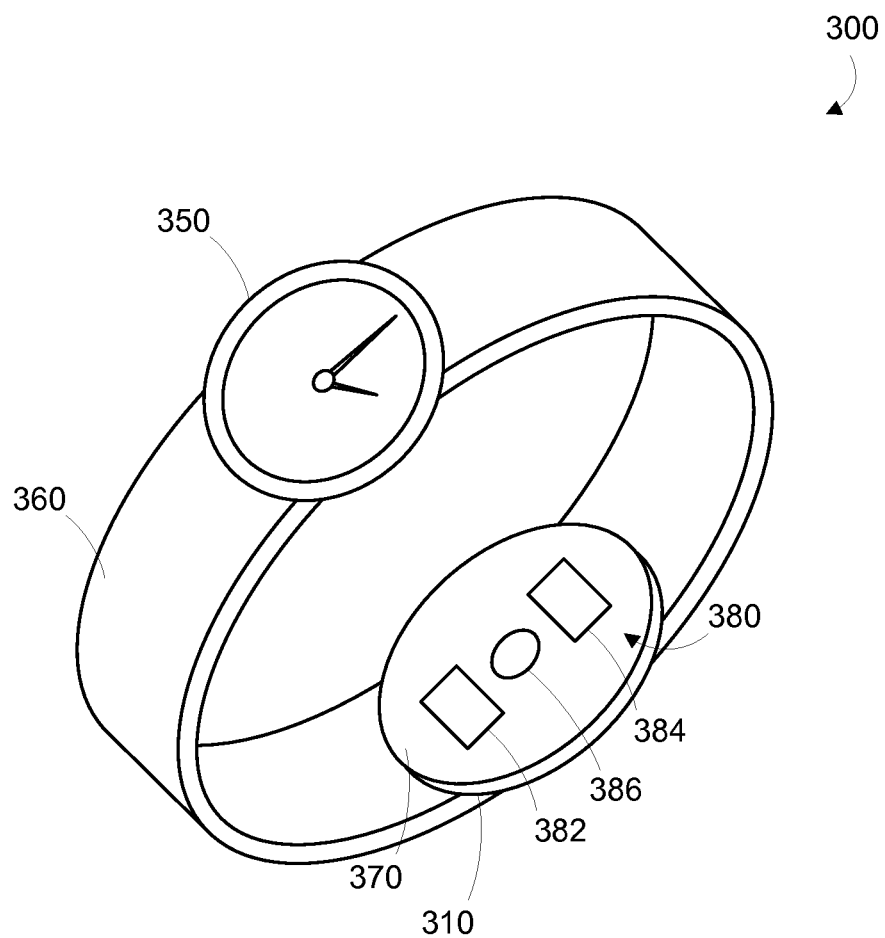
FIG. 3C is a perspective view of an example wrist-mounted device shown in FIGS. 3A and 3B, according to an illustrative embodiment.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
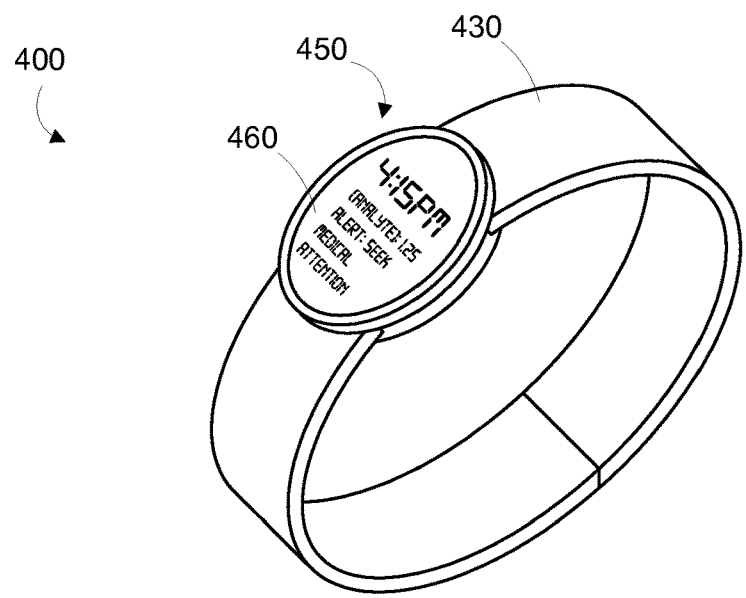
FIG. 4A is a perspective view of an example wrist-mounted device, according to an illustrative embodiment.
Figure 4B:
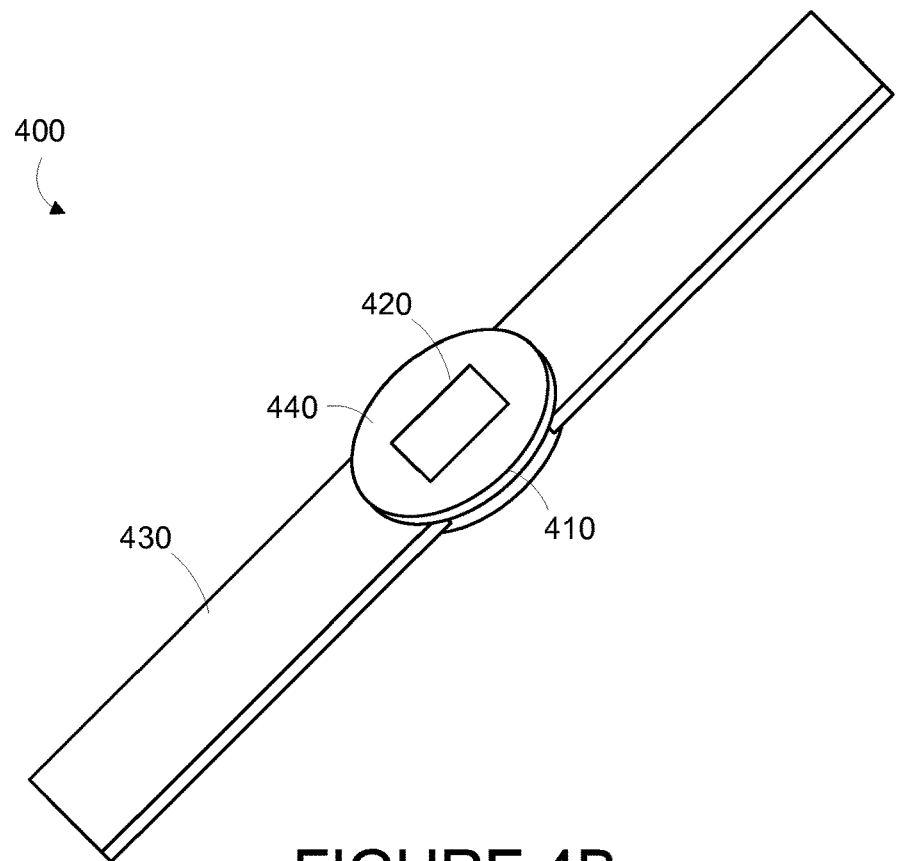
FIG. 4B is a perspective bottom view of an example wrist-mounted device shown in FIG. 4A, according to an illustrative embodiment.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
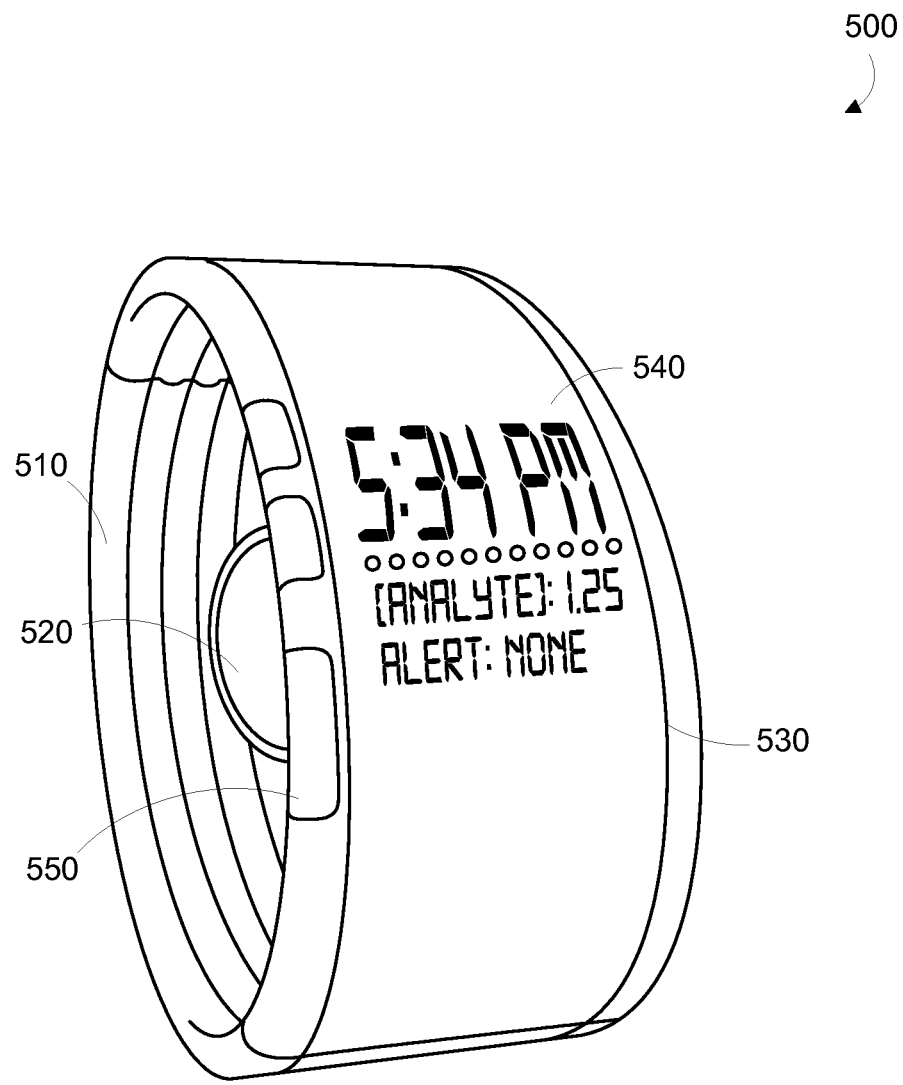
FIG. 5 is a perspective view of an example wrist-mounted device, according to an illustrative embodiment.
Figure 6:
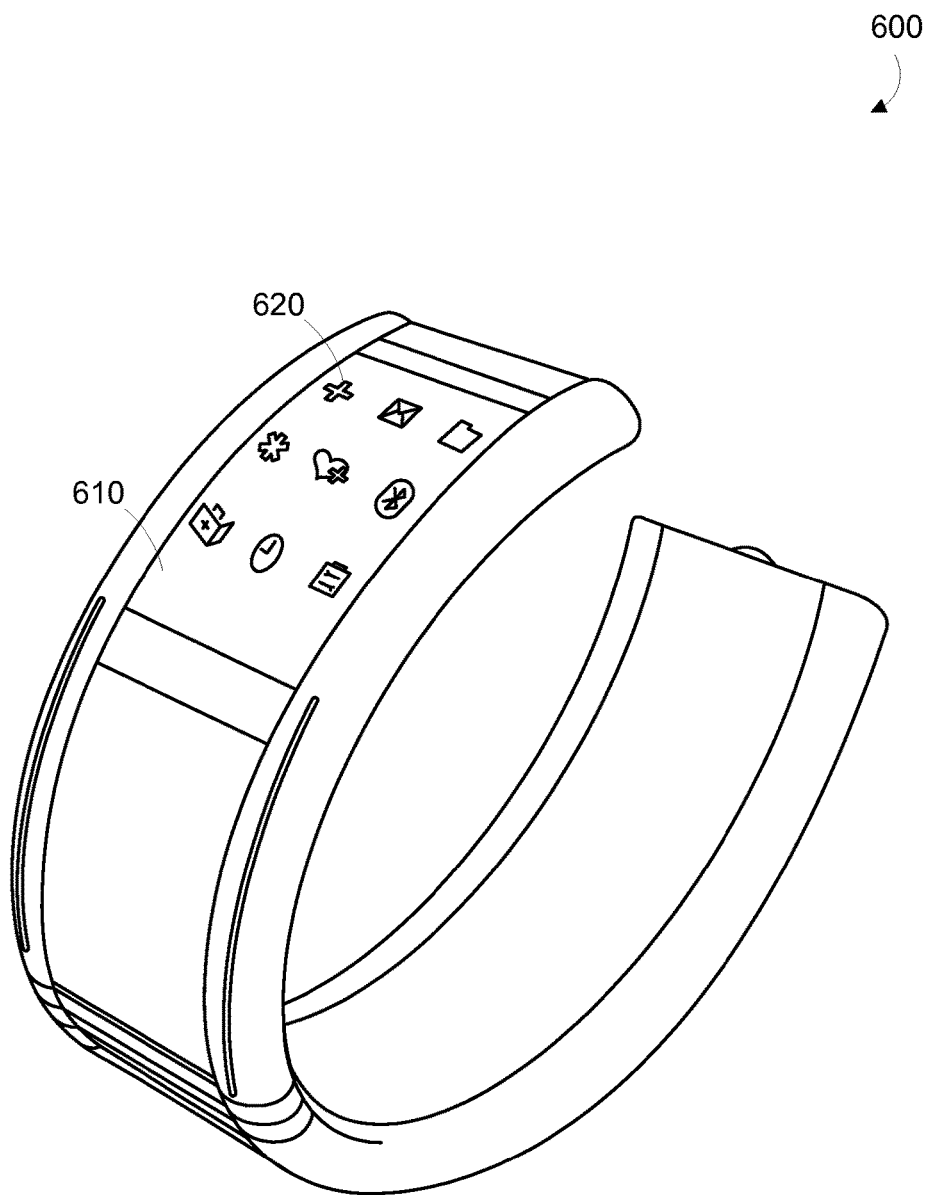
FIG. 6 is a perspective view of an example wrist-mounted device, according to an illustrative embodiment.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health state.

Figure 7:
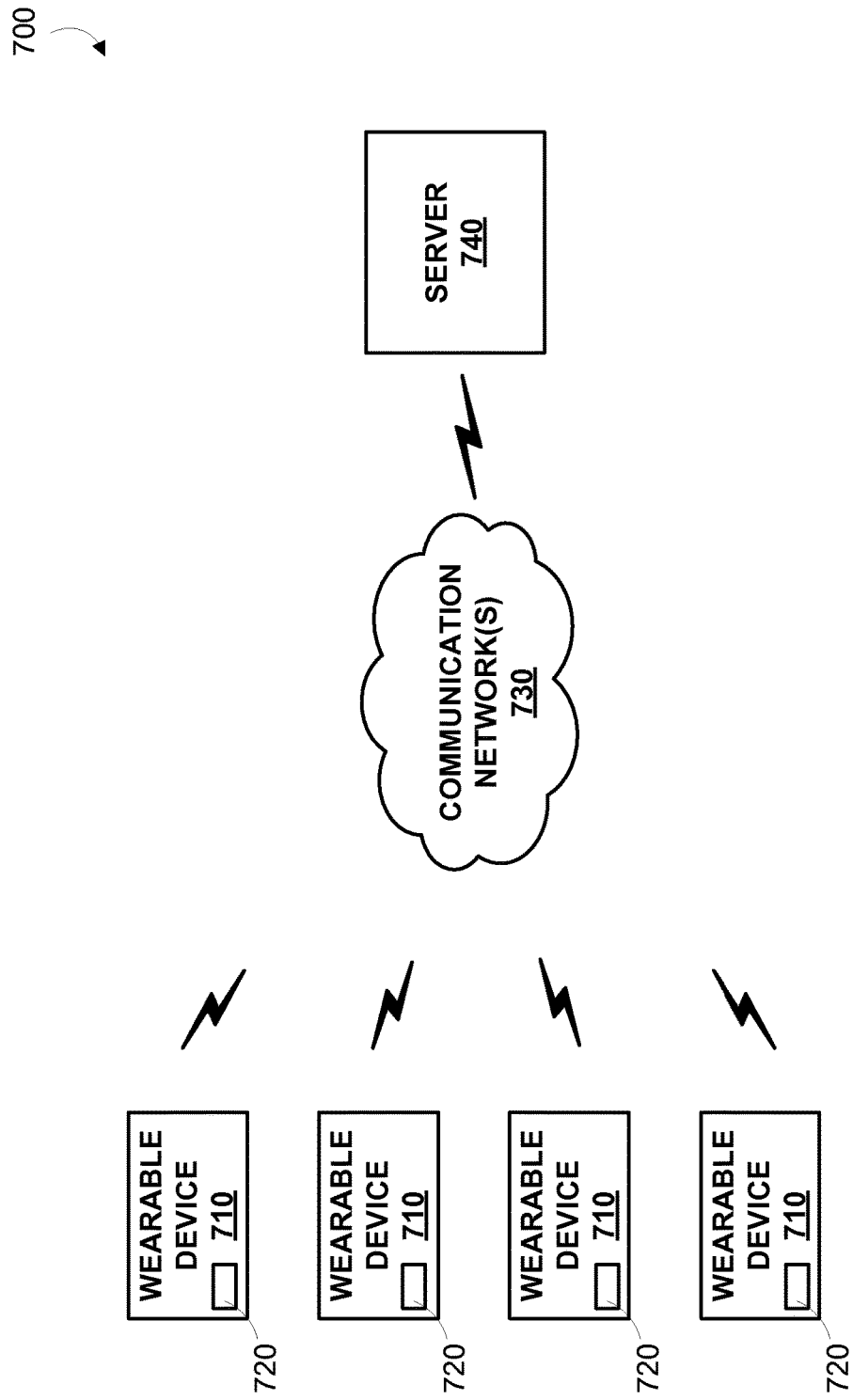
FIG. 7 is a block diagram of an example system that includes a plurality of wearable devices in communication with a server, according to an illustrative embodiment.

FIG. 7 is a simplified schematic of a system including one or more wearable devices 700. The one or more wearable devices 710 may be configured to transmit data via a communication interface 720 over one or more communication networks 730 to a remote server 740. In one embodiment, the communication interface 720 includes a wireless transceiver for sending and receiving communications to and from the server 740. In further embodiments, the communication interface 720 may include any means for the transfer of data, including both wired and wireless communications. For example, the communication interface may include a universal serial bus (USB) interface or a secure digital (SD) card interface. Communication networks 730 may be any one of may be one of: a plain old telephone service (POTS) network, a cellular network, a fiber network and a data network. The server 740 may include any type of remote computing device or remote cloud computing network. Further, communication network 730 may include one or more intermediaries, including, for example wherein the wearable device 710 transmits data to a mobile phone or other personal computing device, which in turn transmits the data to the server 740.

In addition to receiving communications from the wearable device 710, such as collected physiological parameter data and data regarding health state as input by the user, the server may also be configured to gather and/or receive either from the wearable device 710 or from some other source, information regarding a wearer's overall medical history, environmental factors and geographical data. For example, a user account may be established on the server for every wearer that contains the wearer's medical history. Moreover, in some examples, the server 740 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. ILLUSTRATIVE ELECTRONICS PLATFORM FOR A WEARABLE DEVICE

Figure 8:
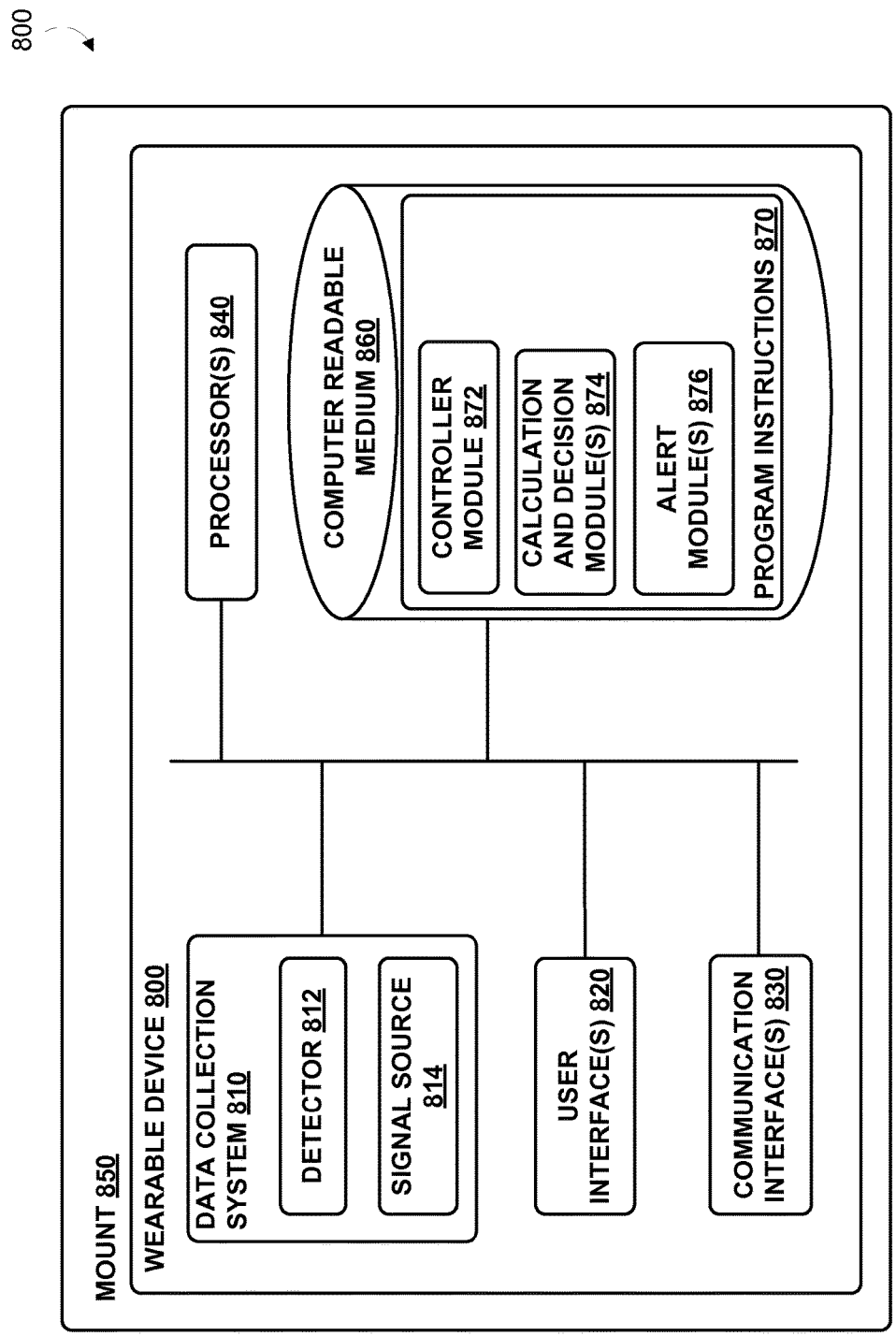
FIG. 8 is a functional block diagram of an example wearable device, according to an illustrative embodiment.

FIG. 8 is a simplified block diagram illustrating the components of a wearable device 800, according to an example embodiment. Wearable device 800 may take the form of or be similar to one of the wrist-mounted devices 200, 300, 400, 500, 600, shown in FIGS. 2A, 2B, 3A-3C, 4A, 5, and 6. However, wearable device 800 may also take other forms, such as an ankle, waist, or chest-mounted device. Alternatively, wearable device 800 may be positioned on various parts of a wearer's body using, for instance, an adhesive.

FIG. 8 shows an example of a wearable device 800 having a data collection system 810, a user interface 820, communication platform 830 for transmitting data to a server, and processor(s) 840. The components of the wearable device 800 may be disposed on a mount 850 for mounting the device to an external body surface where a portion of subsurface vasculature is readily observable.

Processor 840 may be a general-purpose processor or a special purpose processor (e.g., digital signal processors, application-specific integrated circuits, etc.). The one or more processors 840 may be configured to execute computer-readable program instructions 870 that are stored in the computer readable medium 860 and are executable to provide the functionality of a wearable device 800 described herein.

The computer readable medium 860 may include or take the form of one or more non-transitory, computer-readable storage media that may be read or accessed by at least one processor 840. The one or more computer-readable storage media may include volatile and/or non-volatile storage components, such as optical, magnetic, organic or other memory or disc storage, which may be integrated in whole or in part with at least one of the one or more processors 840. In some embodiments, the computer readable medium 860 may be implemented using a single physical device (e.g., one optical, magnetic, organic or other memory or disc storage unit), while in other embodiments, the computer readable medium 860 may be implemented using two or more physical devices.

Data collection system 810 includes a detector 812 and, in some embodiments, a signal source 814. As described above, detector 812 may include one or more detectors configured to detect at least one physiological parameter, which may include parameters that may relate to the health of the person wearing the wearable device 800. For example, the detector 812 may be configured to measure blood pressure, pulse rate, skin temperature, etc. Detector 812 may be configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 810 further includes a signal source 814 for transmitting an interrogating signal that can penetrate the wearer's skin into the portion of subsurface vasculature. In general, signal source 814 may generate an interrogation signal that may, in turn, for example through interactions with a target analyte, produce a response signal that may be detected by one or more of the detectors 812. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the functionalized particles include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812 and signal source 814. For example, the controller 872 may activate signal source 814 and/or detector 812 during one or more pre-set measurement periods. In particular, the controller module 872 can include instructions for controlling the signal source 814 to transmit an interrogating signal at preset measurement times and controlling the detector 812 to receive data representative of response signals transmitted from the portion of subsurface vasculature in response to the interrogating signals transmitted at the preset measurement times.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the wearable device 800. The communication interface 830 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

Calculation and decision module 872 may include instructions for receiving data from the data collection system 810 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 872 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 872 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of the wearer of the device, that may be necessary in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Although wearable device 800 is shown in FIG. 8 with only one signal source (signal source 814) and one detector (detector 812), it is to be understood that wearable device 800 could include a plurality of signal sources and/or a plurality of detectors. For example, wearable device 800 could include first and second signal sources or first and second detectors, as described below in relation to FIG. 10.

Figure 9:
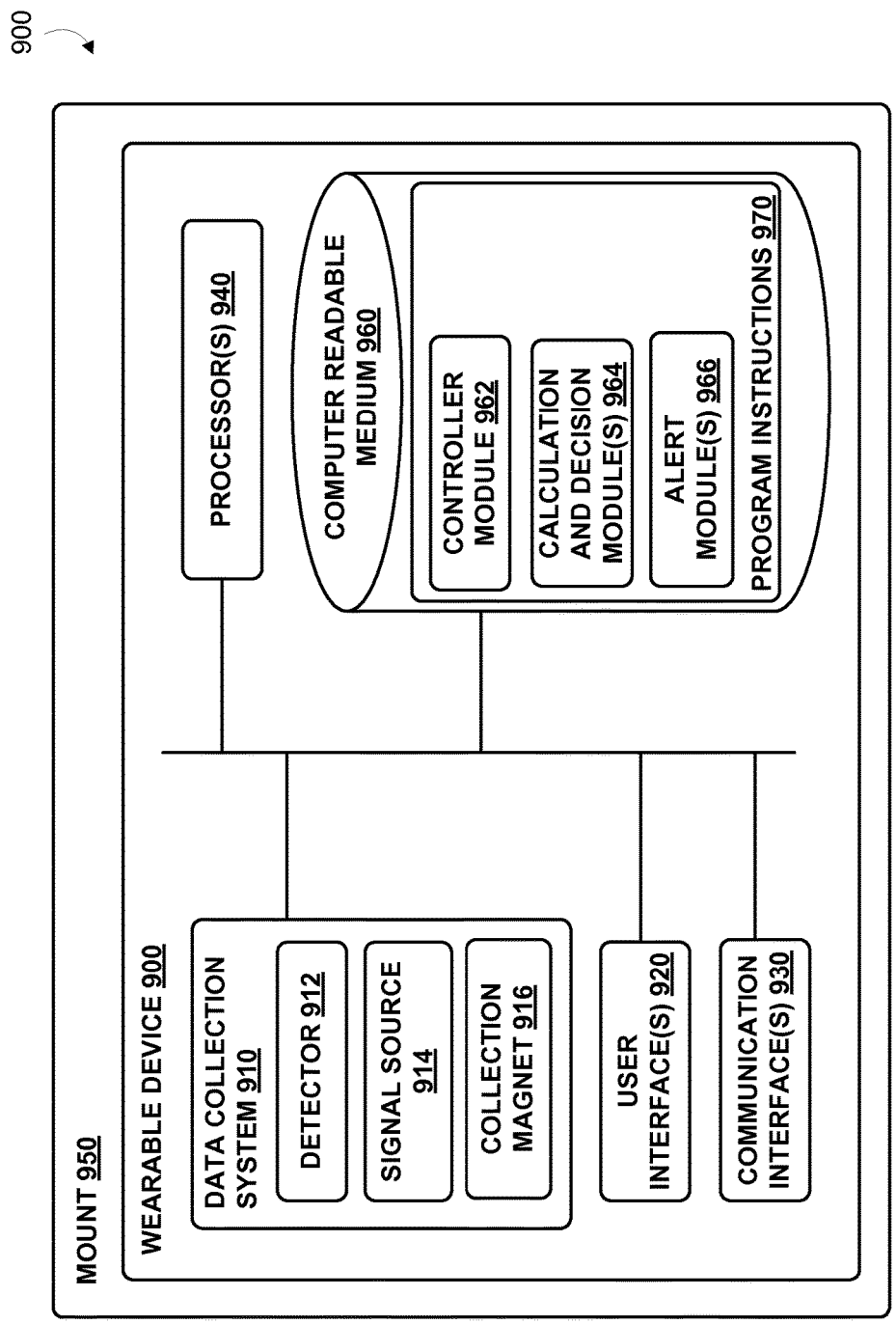
FIG. 9 is a functional block diagram of an example wearable device, according to an illustrative embodiment.

FIG. 9 is a simplified block diagram illustrating the components of a wearable device 900, according to an example embodiment. Wearable device 900 is the same as wearable device 800 in all respects, except that the data collection system 910 of wearable device 900 further includes a collection magnet 916. In this example, the collection magnet 916 may be used to locally collect functionalized magnetic particles present in an area of subsurface vasculature proximate to the collection magnet 916. As described above, collection magnet 916 is configured to direct a magnetic field into a portion of subsurface vasculature sufficient to cause functionalized magnetic particles to collect in a lumen of the portion of subsurface vasculature.

Wearable device 900 includes a data collection system 910, which includes a detector 912, a signal source 914 (if provided) and a collection magnet 916, a user interface 920, a communication interface 930, a processor 940 and a computer readable medium 960 on which program instructions 970 are stored. All of the components of wearable device 900 may be provided on a mount 950. In this example, the program instructions 970 may include a controller module 962, a calculation and decision module 964 and an alert module 966 which, similar to the example set forth in FIG. 8, include instructions to perform or facilitate some or all of the device functionality described herein. Controller module 962 further includes instructions for operating collection magnet 916. For example, controller module 962 may include instructions for activating collection magnet during a measurement period, for a certain amount of time.

Although wearable device 900 is shown in FIG. 9 with only one signal source (signal source 914) and one detector (detector 912), it is to be understood that wearable device 900 could include a plurality of signal sources and/or a plurality of detectors. For example, wearable device 900 could include first and second signal sources or first and second detectors, as described below in relation to FIG. 10.

IV. ILLUSTRATIVE FUNCTIONALIZED PARTICLES

In some examples, the wearable devices described above obtain at least some of the health-related information by detecting the binding of a clinically-relevant analyte to functionalized particles, for example, microparticles or nanoparticles. The particles can be functionalized by covalently attaching a bioreceptor designed to selectively bind or otherwise recognize a particular clinically-relevant analyte. For example, particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The functionalized particles can be introduced into the person's blood stream by injection, ingestion, inhalation, transdermally, or in some other manner.

The clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with a bioreceptor that will selectively bind to this target analyte.

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of functionalized particles into the vasculature or body fluids.

Bioreceptors can be used in diagnostic procedures, or even in therapy to destroy a specific target, such as antitumor therapy or targeted chemotherapy. The particles may be designed to remove from the body or destroy the target analyte once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, tryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the functionalized particles to a target analyte may be detected with or without a stimulating signal input. The term "binding" is understood in its broadest sense to include any detectable interaction between the receptor and the target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

V. ILLUSTRATIVE METHODS FOR REDUCING NOISE IN A WEARABLE DEVICE

Figure 10:
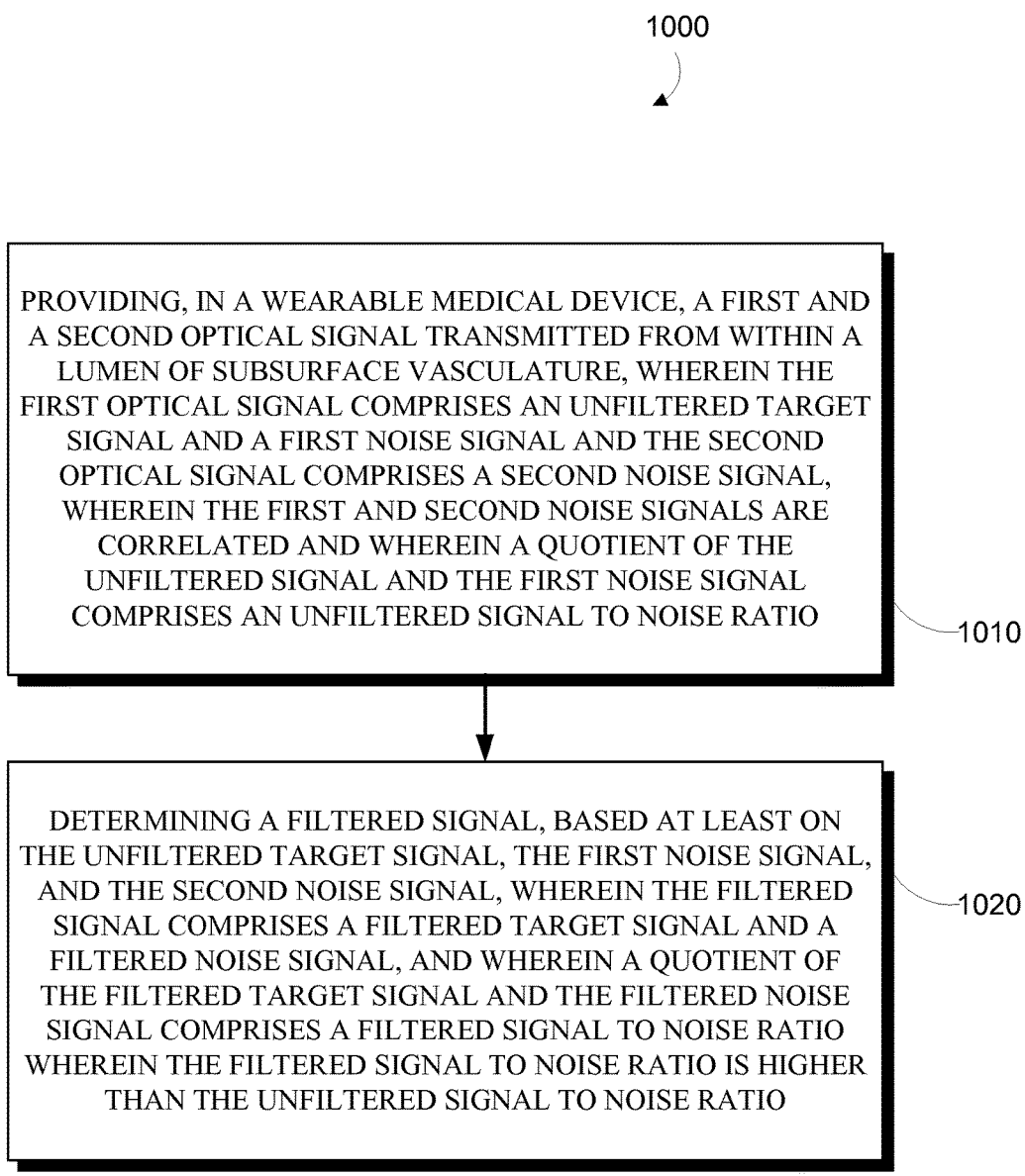
FIG. 10 is a flowchart of an example method for operating a wearable device, according to an illustrative embodiment.

FIG. 10 is a flowchart of a method 1000 for reducing the influence of noise when taking non-invasive, in vivo, real-time measurements of physiological parameters using a wearable device. Block 1010 includes providing, in a wearable medical diagnostic device, a first and a second optical signal transmitted from within a lumen of subsurface vasculature. The first optical signal includes an unfiltered target signal and a first noise signal and the second optical signal includes a second noise signal. The first and second noise signals are correlated and a quotient of the unfiltered target signal and the first noise signal includes an unfiltered signal to noise ratio. Block 1020 includes determining a filtered signal, based at least on the unfiltered target signal, the first noise signal, and the second noise signal. The filtered signal includes a filtered target signal and a filtered noise signal. A quotient of the filtered target signal and the filtered noise signal includes a filtered signal to noise ratio wherein the filtered signal to noise ratio is higher than the unfiltered signal to noise ratio.

In an illustrative embodiment, the wearable device may be mounted to a body surface of a human subject, wherein the body surface is proximate to a portion of subsurface vasculature. The wearable device, via a signal source, may transmit an interrogating signal into the portion of subsurface vasculature. In some examples, a response signal is generated in response to the interrogating signal. For instance, functionalized particles may be configured to bind to the clinically-relevant analyte and may comprise a receptor, such as an antibody. The term "bind" may also include any detectable interaction between the clinically-relevant analyte and the functionalized particles.

The wearable device, via at least one detector, may detect the response signal transmitted from the portion of subsurface vasculature, wherein the response signal is related to binding of a clinically-relevant analyte to functionalized particles present in a lumen of the subsurface vasculature. Additionally or alternatively, the response signal may include optical measurements based on transmission, reflection, or absorbance of light. The response signal may be considered as the first optical signal and may include components based on the response signal as well as noise. In other words, the response signal may be described as including the unfiltered target signal and the first noise signal. In some embodiments, the response signal may include the output of the one or more detectors.

The second optical signal may be detected via at least one detector. The second optical signal includes the second noise signal, which is correlated to the first noise signal. Further, the second optical signal may, but need not, include other components related to the response signal. The first and second noise signals may be correlated if the noise signal components include commonly correlated noise types such as: external noise pick-up, capacitive or inductive coupling, ground loops, scanning noise, or power source noise (e.g. 60 Hz hum). Additionally or alternatively, the first and second noise signals may be correlated based on their variance, distribution, and spectral density. In other words, the first and second noise signals may be correlated if the signals resemble one another and/or one of the noise signals may be predicted based on the other. The first and second noise signals could be positively and/or negatively correlated in one or both of time and state. Other types of correlated noise are possible and contemplated herein.

Noise sources that may contribute to the first and second noise signals may include, but are not limited to, those associated with variable optical coupling to skin or tissue, variation in optical properties of skin or tissue over time due to changes in humidity, temperature, hydration, variations in optical properties between individuals, variations in ambient light sources into detectors, and instrument and detector noise, which may include electrical noise, radio frequency or magnetic interference noise, or noise caused by mechanical movement of the detector or its components. Noise sources may be present both within the wearable medical diagnostic device as well as external to the device.

Determining a filtered signal may include various signal processing, or "denoising", algorithms. Generally, methods contemplated herein include techniques that separate the target signal from noise signals. In an illustrative embodiment, subtraction of a "background" noise signal may be performed. In other words, the second optical signal may be subtracted from the first optical signal. In another embodiment, when a detector array is utilized, demosaicing may be performed based on the correlation between the first and second noise signals. Alternatively or additionally, methods herein may include denoising algorithms known in the art such as the Bayesian Least Squares GSM, Probshrink, or Non Local Means (NLMS) methods. Other methods operable to separate a target signal from a noise signal are contemplated within the scope of this disclosure.

Upon determining a filtered signal, the wearable device may then determine the presence, absence and/or a concentration of the clinically-relevant analyte based on the response signal and whether a medical condition is indicated based on at least the presence, absence and/or concentration of the clinically-relevant analyte. Further, in examples where the functionalized particles are magnetic, the wearable device may further direct a magnetic field into the portion of subsurface vasculature, the magnetic field being sufficient to cause the functionalized magnetic particles to collect in a lumen of the portion of subsurface vasculature.

The wearable medical diagnostic device may carry out Block 1010 and Block 1020 of method 1000 in various ways. For example, in an effort to separate out noise from the response signal, several different noise-reduction measurement techniques may be utilized.

In an illustrative embodiment, the medical diagnostic device may include a first detector and a second detector and a source configured to illuminate an analyte within the lumen. The analyte, which may include a fluorophore, may be configured to emit emission light at a known wavelength and/or set of wavelengths upon illumination by the source. Thus, method 1000 may optionally include spectrally separating at least a portion of the emission light into at least a first spectral band and a second spectral band. For example, the fluorophore may be configured to emit within the first spectral band while the autofluorescence of the illuminated tissue may occur within the second spectral band. In such a scenario, the first optical signal (obtained by the first detector) may include a portion of the first spectral band and the second optical signal (obtained by the second detector) may include a portion of the second spectral band. Spectral separation may be performed using optical band pass filters or using a grating spectrometer. Determining the filtered signal may include subtracting the autofluorescence signal portion from the target signal portion. Alternatively, a fluorophore need not be used. For example, the autofluorescence of different tissues may occur within different wavebands, which may then be spectrally separated using the above method. As a further alternative, the second spectral band may be chosen to coincide with the emission spectrum of the autofluorescence. Other choices are possible for the first and the second spectral bands.

In another illustrative embodiment, the wearable diagnostic device may include a detector and a first and a second source. The first and second sources may be configured to illuminate the analyte within the lumen at a first and second wavelength (or waveband), respectively. In such a scenario, the method 1000 may optionally include periodically illuminating the analyte with the first source at a given period and a given duty cycle. Generally, the duty cycle may be configured to be less than one. The method 1000 may optionally include periodically illuminating the analyte with the second source for at least a portion of the given period while the first source is not illuminating the analyte. For example, the first and second sources may alternate with a 50% duty cycle. The frequency may range from mHz to tens of kHz. The method 1000 may optionally include detecting the first optical signal with the detector while the analyte is illuminated by the first source and detecting the second optical signal with the detector while the analyte is illuminated by the second source. In some example embodiments, the first source may be configured to substantially optically excite the analyte of interest while the second source may be configured to substantially not optically excite the analyte. Alternatively, the first and second sources may be configured to substantially optically excite the analyte to different respective wavelengths. Further, while a simple alternating illumination technique is disclosed above, more complex pulse sequences, such as pulse code modulation schemes, may be used to optimize duty cycle or to improve the separation of noise from the signal of interest.

In yet another illustrative embodiment, the wearable diagnostic device may include a detector and a source. In such a scenario, a primary contrast agent and a normalization contrast agent may be introduced into the lumen. The primary contrast agent may be configured to fluoresce at a first spectral maximum and the normalization contrast agent may be configured to fluoresce at a second spectral maximum. In such an embodiment, the method 1000 may optionally include illuminating the lumen with the source, detecting the first optical signal substantially at the first spectral maximum, and detecting the second optical signal substantially at the second spectral maximum. A spectrometer may be used to obtain the spectral information about the emission signal in response to the source illumination. Additionally or alternatively, the normalization contrast agent may be configured to provide a calibration reference for an optical coupling factor between the detector and the skin surface. For example, a "baseline spectra" may be obtained after the normalization contrast agent is introduced into the lumen, but before the primary contrast introduced into same. The normalization contrast agent may be introduced into circulation and/or may alternatively be introduced into the skin as a "tattoo" such that it is substantially immobile under the detection area. A further marker or probe utilizing the normalization contrast agent may be introduced to serve as a calibration guide for techniques that involve, for instance, adaptive optics or spatially modulated light.

In a further illustrative embodiment, the lumen may include a first and a second portion and the wearable medical diagnostic device may include a source configured to illuminate at least the first and second portions at a spectral illumination maximum. In such a scenario, the method 1000 may optionally include illuminating the first and second portions of the lumen with the source so as to cause a first portion emission and a second portion emission. The method 1000 may also include detecting the first optical signal from the first portion emission (e.g., with a first detector) and detecting the second optical signal from the second portion emission (e.g., with a second detector). In other words, two or more spatially separated detectors may obtain optical signals from various locations along the lumen. The two or more spatially separated detectors may include an array of photodiodes or a multi-element detector. Accordingly, noise may be separated from the response signal when the noise signal contributions from the various locations are correlated. Optionally, such a scenario need only include one detector configured to detect the first portion emission as distinct from the second portion emission. That is, the detector may be moved to be proximate to the first and second portions of the lumen or light from the respective portions of the lumen may otherwise be distinctly transmitted to the detector.

In another illustrative embodiment, the wearable medical diagnostic device may include a detector wherein illuminating the first and second portions of the lumen includes illuminating the first and second portions of the lumen at a first time and a second time, respectively. In such a scenario, the method 1000 may include the detector detecting the first optical signal during the first time and may additionally include the detector detecting the second optical signal during the second time. Put another way, various elements of method 1000 may be carried out at different times so as to determine a filtered signal.

In yet another illustrative embodiment, the wearable medical diagnostic device may include a detector and a source. The method 1000 may also include illuminating the lumen with the source, modulating the first and/or second noise signals, and then detecting the first and second optical signals with the detector. Modulating the first and second noise signals may include modulating the source illumination in a way that need not substantially change the emission of the analyte of interest. For example, the source illumination may increase in intensity at a wavelength or waveband different from a waveband that may induce emission from an analyte such as a fluorophore. In so doing, the emission of background tissues, for instance, may be modulated. Signal processing may be used to subtract or otherwise separate the noise signals from the signal of interest. Alternatively or additionally, non-optical methods could be used to modulate the background noise signal. For example, changing the temperature of the surrounding tissues may affect emission, absorption, and/or reflective properties of said tissues. In such a scenario, the first and second noise signals may be affected or modulated substantially independent of the signal of interest. In another example, acoustic modulation of surrounding tissues may change the emission, absorption, and/or reflective properties of the tissues. Again, the acoustic modulation of surrounding tissues may affect the first and second noise signals substantially independent of the signal of interest. Other ways of modulating the background noise signals will be evident to those with skill in the art and may include other optical and non-optical means for changing the background noise signal substantially independent from the signal of interest.

The method 1000 may include other ways of performing gradiometric measurements. For example, any combination of emission unmixing or excitation unmixing may be included in the method 1000. Furthermore, any combination of methods known in the art to provide background normalization and/or background modulation may be included in the method 1000.

VI. ILLUSTRATIVE WEARABLE MEDICAL DIAGNOSTIC SYSTEM WITH NOISE REDUCTION

FIGS. 11A-11B, 12A-12B, and 13A-13B are partial cross-sectional side views of a human wrist illustrating the operation of various examples of a wrist-mounted device. In the example shown in FIGS. 11A and 11B, the wrist-mounted device 1100 includes a measurement platform 1110 mounted on a strap or wrist-band 1120 and oriented on the anterior side 1190 of the wearer's wrist. Measurement platform 1110 is positioned over a portion of the wrist where subsurface vasculature 1130 is easily observable. Functionalized particles 1140 have been introduced into a lumen of the subsurface vasculature by one of the means discussed above. In this example, measurement platform 1110 includes a data collection system having both a detector 1150 and a signal source 1160. FIG. 11A illustrates the state of the subsurface vasculature when measurement device 1100 is inactive. The state of the subsurface vasculature during a measurement period is illustrated in FIG. 11B. At this time, signal source 1160 is transmitting an interrogating signal 1162 into the portion of subsurface vasculature and detector 1150 is receiving a response signal 1152 generated in response to the interrogating signal 1162. The response signal 1152 is related to the binding of a clinically-relevant analyte present in the subsurface vasculature to the functionalized particles 1140. As described above, in some embodiments, an interrogating signal may not be necessary to generate a response signal related to the binding of an analyte to the functionalized particles.

Similar to the system depicted in FIGS. 11A and 11B, FIGS. 12A and 12B illustrate a wrist-mounted device 1200 including a measurement platform 1210 mounted on a strap or wristband 1220 and oriented on the anterior side 1290 of the wearer's wrist. In this example, measurement platform 1210 includes a data collection system having a detector 1250, a signal source 1260 and a collection magnet 1270. FIG. 12A illustrates the state of the subsurface vasculature when measurement device 1200 is inactive. The state of the subsurface vasculature when measurement device 1200 is active during a measurement period is illustrated in FIG. 12B. At this time, collection magnet 1270 generates a magnetic field 1272 sufficient to cause functionalized magnetic particles 1240 present in a lumen of the subsurface vasculature 1230 to collection in a region proximal to the magnet 1270. Signal source 1260 transmits an interrogating signal 1262 into the portion of subsurface vasculature and detector 1250 is receiving a response signal 1252 generated in response to the interrogating signal 1262. The response signal 1252 is related to the binding of a clinically relevant analyte present in the subsurface vasculature to the functionalized magnetic particles 1240. As described above, in some embodiments, an interrogating signal may not be necessary to generate a response signal related to the binding of an analyte to the functionalized magnetic particles.

FIGS. 13A and 13B illustrate a further embodiment of a wrist-mounted device 1300 having a measurement platform 1310 disposed on a strap 1320, wherein the detector 1350 and signal source 1360 are positioned on the posterior side 1390 of the wearer's wrist and the collection magnet 1370 is disposed on the anterior side 1380 of the wearer's wrist. Similar to the embodiments discussed above, FIG. 13A illustrates the state of the subsurface vasculature when measurement device 1300 is inactive. The state of the subsurface vasculature when measurement device 1300 is active during a measurement period is illustrated in FIG.

13B. At this time, collection magnet 1370 generates a magnetic field 1232 sufficient to cause functionalized magnetic particles 1340 present in a lumen of the subsurface vasculature 1330 to collection in a region proximal to the magnet 1370. Signal source 1360 transmits an interrogating signal 1362 into the portion of subsurface vasculature and detector 1350 is receiving a response signal 1352 generated in response to the interrogating signal 1262. The response signal 1352 is related to the binding of a clinically relevant analyte present in the subsurface vasculature to the functionalized magnetic particles 1340. As described above, in some embodiments, an interrogating signal may not be necessary to generate a response signal related to the binding of an analyte to the functionalized magnetic particles.

Both FIGS. 12B and 13B illustrate the path of the interrogating signal (1262, 1362) transmitted by the signal source (1260, 1360) and the responsive signal (1252, 1352) detected by the detector (1250, 1350) essentially overlapping over a portion of subsurface vasculature. In some examples, the signal source (1260, 1360) and the detector (1250, 1350) may be angled towards each other so that they are interrogating and detecting from essentially the same area of subsurface vasculature. However, in some instances, such as in the example shown in FIG. 11B, the paths of the interrogating signal (1262, 1362) transmitted by the signal source (1260, 1360) and the responsive signal (1252, 1352) detected by the detector (1250, 1350) may not overlap.

The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, particles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

Figure 14:
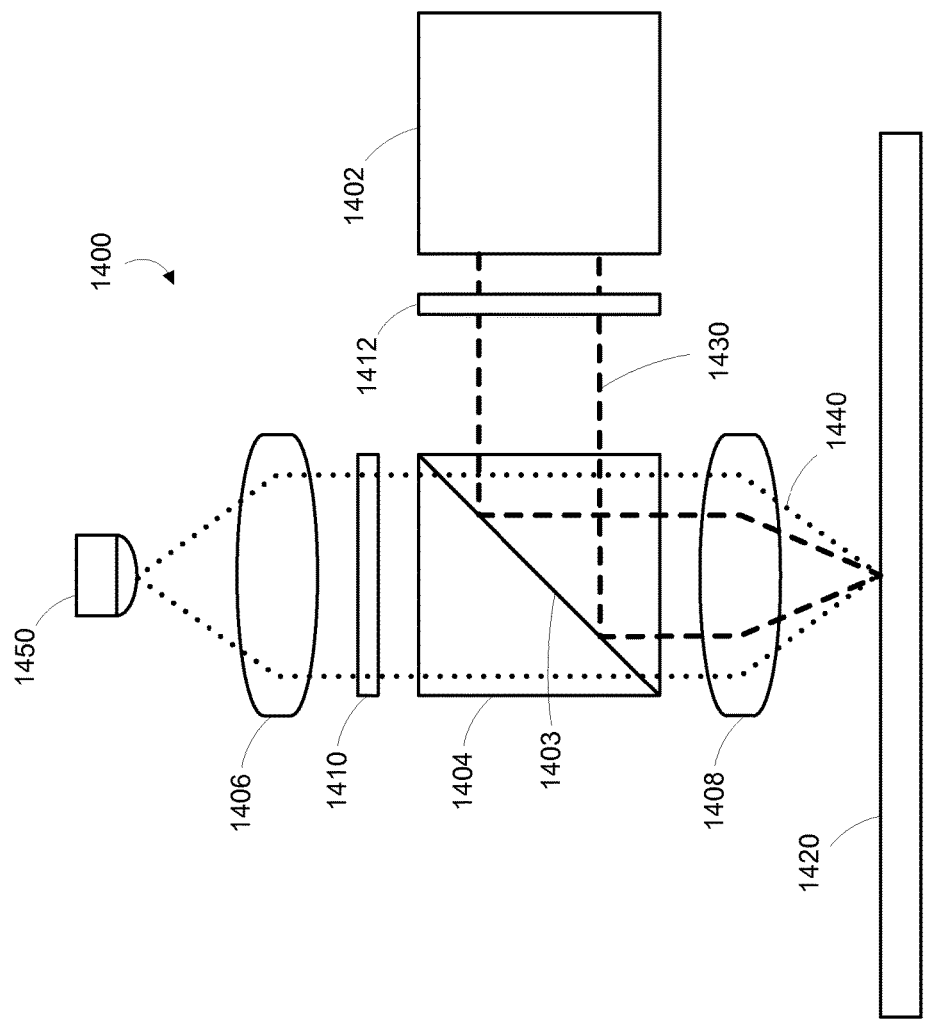
FIG. 14 is a functional block diagram of a wearable medical diagnostic system with noise reduction, according to an illustrative embodiment.

FIG. 14 is a functional block diagram of a wearable medical diagnostic system with noise reduction 1400, according to an illustrative embodiment. The wearable medical diagnostic system 1400 may include a source 1402, filters 1410 and 1412, a dichroic beamsplitter 1404, lenses 1406 and 1408, a target location 1420, and a detector 1450. The source 1402 may be configured to transmit an interrogating signal 1430 via the dichroic beamsplitter 1404, and lens 1408 towards the target location 1420. The dichroic beamsplitter 1404 may be configured to reflect and/or transmit light based, at least in part, on the wavelength of such light. For example, the dichroic beamsplitter 1404 may be configured to reflect the interrogating signal 1430, which may include light at first wavelength and/or a first waveband, from source 1402 towards the target location 1420.

The source 1402 may include a laser, a light-emitting diode (LED), or another device configured to produce light. The source 1402 may be configured to produce light at or around a particular wavelength or within a particular waveband. For example, the source 1402 may be configured to emit light at a wavelength known to cause a given fluorophore to emit light at a second wavelength or second waveband. The light from source 1402 may be substantially collimated, such as from a laser. Alternatively, the light from source 1402 may be collected and collimated and/or focused so as to illuminate target location 1420. The source 1402 may be configured to provide continuous illumination. Alternatively, source 1402 may provide pulsed or otherwise intermittent light. In an illustrative embodiment source 1402 may include a LED that provides light substantially in the infrared spectral band. Source 1402 may additionally be configured to provide illumination at more than one wavelength or over more than one waveband. Yet further, source 1402 may represent more than one light source. For example, source 1402 may be an array of light emitters or may include at least two light sources at spatially-separated locations. In other words, although FIG. 14 depicts one source 1402 and one associated optical path (e.g. illustrated by interrogation signal 1430), multiple sources and/or multiple optical paths could be utilized within the scope of the present disclosure.

In one example, multiple sources 1402 may be configured to spatially modulate the analyte response signal. For example, a spatial modulation may exploit the speed, rotation, size, thermodynamic properties, hydrodynamic properties, etc. of the bound particles, versus unbound particles and other items that are not of interest, travelling near the target location 1440 to distinguish the analyte response signal. For example, an analyte-bound particle is going to have a different size and shape than an unbound particle and, therefore, may travel through the subsurface vasculature a different speed, thereby modulating between bound and unbound particles. In one example, analyte-bound magnetic particles may travel through the subsurface vasculature at a different speed when subject to a magnetic field than unbound magnetic particles. The multiple sources 1402 may be used to exploit this difference in speed to differentiate the analyte response signal from other signals transmitted from the body.

In an illustrative embodiment, a first source and a second source may be configured to illuminate the target location 1420, which may include the location of a target analyte. The first source may be configured to provide light substantially at a first wavelength and the second source may be configured to provide light substantially at a second wavelength. Furthermore, the first source may periodically illuminate the target location 1420 at a given period and a given duty cycle. The second source may periodically illuminate the target location 1420 while the first source is not illuminating the target location 1420. In such a scenario, the detector 1450 may detect the unfiltered target signal and the first noise signal while the target location 1420 is illuminated by the first source. Additionally, the detector 1450 may detect the second noise signal while the target location 1420 is illuminated by the second source.

The target location 1420 may include a lumen of the subsurface vasculature as described herein, for example with reference to FIGS. 11A&B. The target location 1420 may alternatively or additionally include other locations or structures, such as a skin surface, a bone, a blood vessel, a muscle, and/or another part of a body. The target location 1420 may alternatively represent blood, another bodily fluid, or another medium in which analytes of interest may be detected.

When light is emitted or reflected from the target location 1420, a response signal 1440 may be collected by the wearable medical diagnostic system 1400. In an illustrative embodiment, the response signal 1440 may be collected with lens 1408. The dichroic beamsplitter 1404 may be configured to substantially transmit the response signal 1440, which may include a second wavelength and/or a second waveband. In such a scenario, the emitted light may pass substantially through the dichroic beamsplitter 1404 towards the detector 1450. Specifically, the response signal 1440 may pass through emission filter 1410 and may be focused by lens 1406 onto the detector 1450.

Detector 1450 may be configured to sense light at various wavelengths or within various wavebands. For example, detector 1450 may be configured to sense infrared light, visible light, ultraviolet light, and/or any other wavelength or waveband of light.

Filters 1410 and 1412 may be spectral filters configured to block, attenuate, and/or transmit various wavelengths and/or wavebands of light. The filters could be, for example, gratings or prisms. Other types of filters are possible as well.

Although lens 1408 is depicted as focusing the interrogating signal 1430 onto the target location 1420, lens 1408 may affect the interrogating signal 1430 in other ways. For example, lens 1408 may represent a collimating lens. In such a scenario, the collimating lens may be used so as to direct a collimated optical beam towards the target location 1420. Alternatively or additionally, the lens 1408 may represent a spatial light modulator. In such a scenario, the spatial light modulator may be utilized to direct light towards various spatial locations near the target location 1420. Alternatively, the spatial light modulator may be used to modulate or block various portions of the interrogating signal 1430 and/or modulate or block the entire interrogating signal 1430. Furthermore, lens 1408 may represent more than one optical lens. For example, instead of using lens 1408 as a focusing and collection optic, two or more lenses could be utilized to achieve one or more of focusing the interrogating signal 1430 and collecting the response signal 1440. Other optical elements or combinations thereof may be used in place of lens 1408.

Similarly, other optical elements or combinations thereof may be used in place of lens 1406. For example, lens 1406 may represent a spatial light modulator, a collimating lens, a focusing mirror, a plane mirror, or another optical element.

Dichroic beamsplitter 1404 may represent various optical components configured to reflect and/or transmit light based, in part, on the wavelength of the incoming light. In an illustrative embodiment, the dichroic beamsplitter may include a surface 1403 configured to reflect and/or transmit light based on its wavelength. Alternatively, dichroic beamsplitter 1404 may represent a prism or a grating, such as those used in a grating spectrometer.

Figure 15:
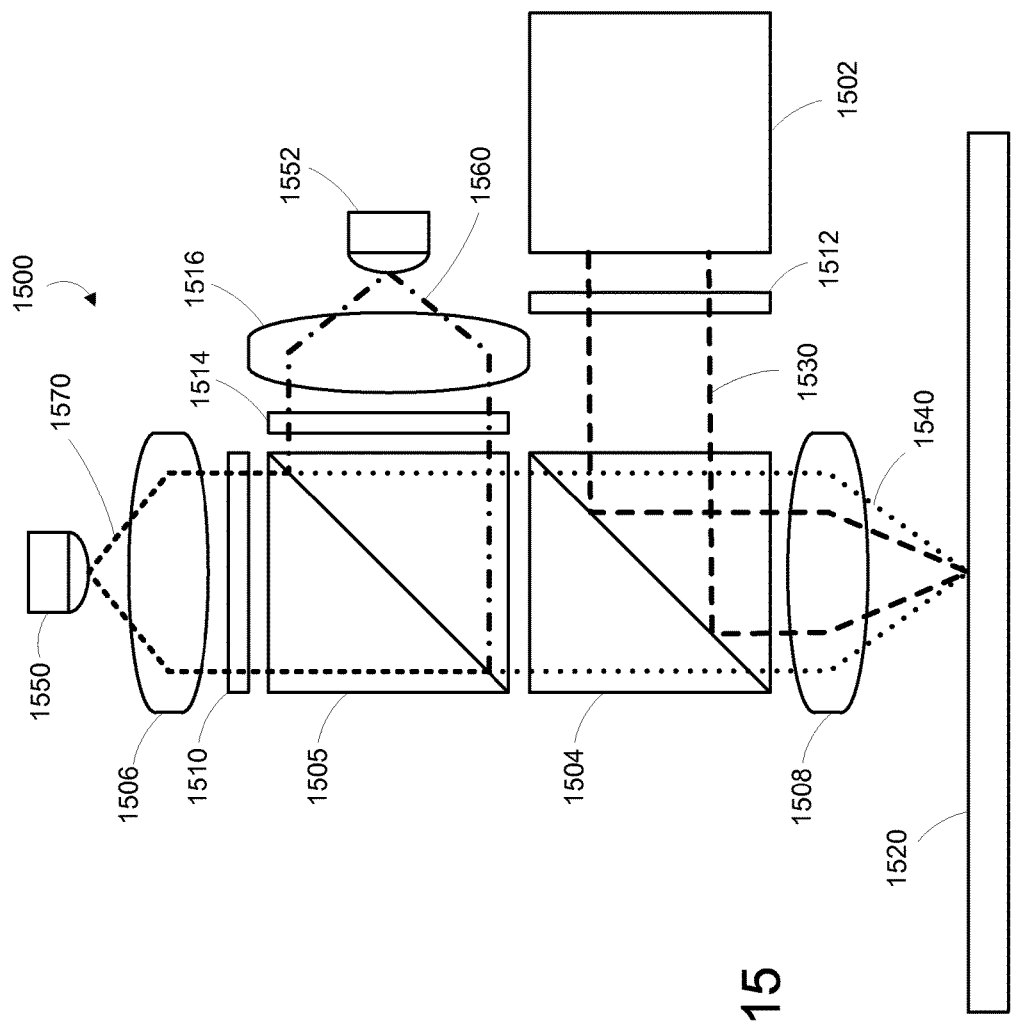
FIG. 15 is a functional block diagram of a wearable medical diagnostic system with noise reduction, according to an illustrative embodiment.

FIG. 15 is a functional block diagram of a wearable medical diagnostic system with noise reduction 1500, according to an illustrative embodiment. Wearable medical diagnostic system 1500 may include a source 1502, filters 1510, 1512, and 1514, lenses 1506, 1508, and 1516, detectors 1550 and 1552, as well as dichroic beamsplitters 1504 and 1505. In an illustrative embodiment, interrogating signal 1530 may be emitted from source 1502. The interrogating signal 1530 may be directed towards a target location 1520 via dichroic beamsplitter 1504 and 1508. The interrogating signal may interact with analytes near the target location 1520. The analytes and/or bound particles may emit light that may be collected as a response signal 1540. The response signal 1540 may be directed towards dichroic beamsplitter 1505 via lens 1508 and dichroic beamsplitter 1504. Dichroic beamsplitter 1505 may reflect and/or transmit a portion of the response signal 1540 towards detector 1550 or detector 1552. For example, dichroic beamsplitter 1505 may be configured to reflect a first portion of response signal 1560 towards detector 1552 based, at least in part, on the wavelength or waveband of the first portion of response signal 1560. Additionally or alternatively, dichroic beamsplitter 1552 may be configured to transmit a second portion of response signal 1570 towards detector 1550 based, at least in part, on the wavelength or waveband of the second portion of response signal 1570.

In another illustrative embodiment, dichroic beamsplitter 1552 may represent a flip mirror or another optical element configured to steer or direct at least a portion of the response signal 1540 towards detector 1550 and/or detector 1552. Similar to system 1400, the optical components depicted in system 1500 may be substituted with one or more other known optical components.

One with skill in the art will recognize that various configurations of the wearable medical diagnostic systems 1400 and 1500 are contemplated within the scope of this disclosure. The depicted configurations are not meant to limit the numerous different optical configurations that may be used to carry out the methods disclosed herein.

The wearable medical diagnostic devices 1400 and 1500 may additionally include a computing device (not shown) configured to determine a filtered signal, based at least on the response signal 1440 and 1540, which may include an unfiltered target signal, a first noise signal, and a second noise signal. The first and second noise signals may be correlated and a quotient of the unfiltered target signal and the first noise signal may include an unfiltered signal to noise ratio. The filtered signal may include a filtered target signal and a filtered noise signal. The computing device may be configured to provide a quotient of the filtered signal and the filtered noise signal. The quotient of the filtered signal and the filtered noise signal may represent a filtered signal to noise ratio. The filtered signal to noise ratio may be higher than an unfiltered signal to noise ratio. In reference to FIG. 10, the wearable medical diagnostic devices 1400 and 1500 may be configured so as to carry out method 1000 and each of the illustrative embodiments disclosed herein.

The first and second signal may include any signal transmitted from something other than what the systems 1400 and 1500 are monitoring, i.e., the target analyte(s). In some examples, the background signal may be generated by other molecules, cells, or particles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In an illustrative embodiment, the computing device may be configured to spectrally separate emission light (e.g. response signal 1540) into a first spectral band and a second spectral band. For example, a first detector (e.g. detector 1550) may be configured to detect light within the first spectral band. In such a scenario, a second detector (e.g. detector 1552) may be configured to detect light within the second spectral band.

In another illustrative embodiment, a lumen may include a primary contrast agent configured to fluoresce at a first spectral maximum. The lumen may additionally include a normalization contrast agent configured to fluoresce at a second spectral maximum. In such a scenario, the computing device may be further configured to receive, via the detector, the unfiltered target signal and the first noise signal at the first spectral maximum. Additionally, the computing device may be further configured to receive, via the detector, the second noise signal at the second spectral maximum.

In yet another illustrative embodiment, the system may be configured to illuminate a first portion and a second portion of the lumen (e.g. designating and illuminating multiple target locations 1540). In such a scenario, illumination may produce first portion emission and second portion emission. Thus, the detector may detect the unfiltered target signal and the first noise signal from the first portion emission. The detector may also detect the second noise signal from the second portion emission.

VII. ILLUSTRATIVE NON-TRANSITIVE COMPUTER READABLE MEDIUM

Some or all of the functions described above and illustrated in FIG. 10 may be performed by a computing device in response to the execution of instructions stored in a non-transitory computer readable medium. The non-transitory computer readable medium may be, for example, a random access memory (RAM), a read-only memory (ROM), a flash memory, a cache memory, one or more magnetically encoded discs, one or more optically encoded discs, or any other form of non-transitory data storage. The non-transitory computer readable medium may also be distributed among multiple data storage elements, which may be remotely located from each other. The computing device that executes the stored instructions may include the processor 940 as described and illustrated in FIG. 9. Additionally or alternatively, the computing device may include another computing device, such as a server in a server network.

The non-transitory computer readable medium may store instructions executable by a computing device (e.g. processor 940 as described in reference to FIG. 9) to cause the computing device to perform any of the functions described herein.

In one example, the functions include receiving, in a wearable medical diagnostic device, a first and a second optical signal transmitted from within a lumen of subsurface vasculature. The first optical signal includes an unfiltered target signal and a first noise signal. The second optical signal includes a second noise signal. The first and second noise signals are correlated. The quotient of the unfiltered target signal and the first noise signal includes an unfiltered signal to noise ratio. The functions further include determining a filtered signal, based at least on the unfiltered target signal, the first noise signal, and the second noise signal. The filtered signal includes a filtered target signal and a filtered noise signal. A quotient of the filtered target signal and the filtered noise signal includes a filtered signal to noise ratio in which the filtered signal to noise ratio is higher than the unfiltered signal to noise ratio.

VIII. CONCLUSION

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
   detecting, by at least one optical detector of a medical diagnostic device, a first optical signal transmitted through a skin surface from within a first portion of a lumen of subsurface vasculature, wherein the first optical signal comprises an unfiltered target signal and a first noise signal;
   detecting, by the at least one optical detector of the device, a second optical signal transmitted through the skin surface from within a second portion of the lumen of the subsurface vasculature, wherein the second optical signal comprises a second noise signal, and wherein the first and second noise signals are correlated and wherein a quotient of the unfiltered target signal and the first noise signal comprises an unfiltered signal to noise ratio; and
   determining a filtered signal, based at least on the unfiltered target signal, the first noise signal, and the second noise signal, wherein the filtered signal comprises a filtered target signal and a filtered noise signal, wherein a quotient of the filtered target signal and the filtered noise signal comprises a filtered signal to noise ratio, wherein determining the filtered signal based at least on the unfiltered target signal, the first noise signal, and the second noise signal comprises determining the filtered signal such that the filtered signal to noise ratio is higher than the unfiltered signal to noise ratio.

2. The method of claim 1 wherein the medical diagnostic device comprises a source configured to illuminate an analyte within the lumen such that the analyte emits emission light, and the method further comprising:
   spectrally separating at least a portion of the emission light into at least a first spectral band and a second spectral band, wherein the first optical signal comprises at least a portion of the first spectral band, wherein detecting the first optical signal comprises using the optical detector to detect the first optical signal.

3. The method of claim 2 wherein the analyte comprises at least one fluorophore that fluoresces within the first spectral band when illuminated by the source.

4. The method of claim 1 wherein the medical diagnostic device comprises a source, the method further comprising:
  illuminating the lumen with the source; and
  modulating the first and second noise signals.

5. The method of claim 1, wherein detecting, by the at least one optical detector, the first optical signal comprises operating a first optical detector at a first location to detect the first optical signal, wherein detecting, by the at least one optical detector, the second optical signal comprises operating a second optical detector at a second location to detect the second optical signal, and wherein the first and second locations differ.

6. The method of claim 1, wherein detecting, by the at least one optical detector, the first optical signal comprises operating a first light source of the device to illuminate the first portion of the lumen of subsurface vasculature, and wherein detecting, by the at least one optical detector, the second optical signal comprises operating a second light source of the device to illuminate the second portion of the lumen of subsurface vasculature.

7. A medical diagnostic device, comprising:
  at least one optical detector configured to detect an unfiltered target signal, a first noise signal, and a second noise signal, wherein the unfiltered target signal and first noise signal are transmitted through a skin surface from within a first portion of a lumen of subsurface vasculature, wherein the second noise signal is transmitted through the skin surface from within a second portion of the lumen of subsurface vasculature, wherein the first and second noise signals are correlated, and wherein a quotient of the unfiltered target signal and the first noise signal comprises an unfiltered signal to noise ratio; and
  a computing device configured to:
    determine a filtered signal, based at least on the unfiltered target signal, the first noise signal, and the second noise signal, wherein the filtered signal comprises a filtered target signal and a filtered noise signal, and wherein a quotient of the filtered target signal and the filtered noise signal comprises a filtered signal to noise ratio, wherein determining the filtered signal based at least on the unfiltered target signal, the first noise signal, and the second noise signal comprises determining the filtered signal such that the filtered signal to noise ratio is higher than the unfiltered signal to noise ratio.

8. The medical diagnostic device of claim 7, wherein the medical diagnostic device further comprises:
  a source configured to illuminate an analyte within the lumen such that the analyte emits emission light, wherein the medical diagnostic device is further configured to:
  spectrally separate at least a portion of the emission light from the first portion of the lumen of subsurface vasculature into at least a first spectral band and a second spectral band, wherein the computing device is further configured to detect at least a portion of the first spectral band with the at least one optical detector.

9. The medical diagnostic device of claim 7, wherein the at least one optical detector comprises a first optical detector that receives, at a first location, the unfiltered target signal and first noise signal from the first portion of the lumen of subsurface vasculature, wherein the at least one optical detector further comprises a second optical detector that receives, at a second location, the second noise signal from the second portion of the lumen of subsurface vasculature, and wherein the first and second locations differ.

10. The medical diagnostic device of claim 7, further comprising a first light source configured to illuminate the first portion of the lumen of subsurface vasculature and a second light source configured to illuminate the second portion of the lumen of subsurface vasculature.

11. A non-transitory computer readable medium having stored therein instructions executable by a computing device to cause the computing device to perform operations comprising:
  detecting, by at least one optical detector in a medical diagnostic device, a first optical signal transmitted through a skin surface from within a first portion of a lumen of subsurface vasculature and a second optical signal transmitted through the skin surface from within a second portion of the lumen of subsurface vasculature, wherein the first optical signal comprises an unfiltered target signal and a first noise signal and the second optical signal comprises a second noise signal, wherein the first and second noise signals are correlated and wherein a quotient of the unfiltered target signal and the first noise signal comprises an unfiltered signal to noise ratio; and
  determining a filtered signal, based at least on the unfiltered target signal, the first noise signal, and the second noise signal, wherein the filtered signal comprises a filtered target signal and a filtered noise signal, and wherein a quotient of the filtered target signal and the filtered noise signal comprises a filtered signal to noise ratio, wherein determining the filtered signal based at least on the unfiltered target signal, the first noise signal, and the second noise signal comprises determining the filtered signal such that the filtered signal to noise ratio is higher than the unfiltered signal to noise ratio.

12. The non-transitory computer readable medium of claim 11, wherein the medical diagnostic device comprises a source configured to illuminate an analyte within the lumen such that the analyte emits emission light, and the operations further comprising:
  causing at least a portion of the emission light to be spectrally separated into at least a first spectral band and a second spectral band; and
  detecting the first optical signal using the optical detector, wherein the first optical signal comprises at least a portion of the first spectral band.

13. The non-transitory computer readable medium of claim 11, wherein detecting, by the at least one optical detector, the first optical signal comprises operating a first optical detector at a first location to detect the first optical signal, wherein detecting, by the at least one optical detector, the second optical signal comprises operating a second optical detector at a second location to detect the second optical signal, and wherein the first and second locations differ.

14. The non-transitory computer readable medium of claim 11, wherein detecting, by the at least one optical detector, the first optical signal comprises operating a first light source of the device to illuminate the first portion of the lumen of subsurface vasculature, and wherein detecting, by the at least one optical detector, the second optical signal comprises operating a second light source of the device to illuminate the second portion of the lumen of subsurface vasculature.

* * * * *